(12) United States Patent
Miller

(10) Patent No.: US 8,029,501 B2
(45) Date of Patent: Oct. 4, 2011

(54) LASER SELECTIVE CUTTING BY IMPULSIVE HEAT DEPOSITION IN THE IR WAVELENGTH RANGE FOR DIRECT-DRIVE ABLATION

(75) Inventor: R. J. Dwayne Miller, Port Credit (CA)

(73) Assignee: Attodyne Inc., Toronto, Ontario (CA)

(*) Notice: Subject to any disclaimer, the term of this patent is extended or adjusted under 35 U.S.C. 154(b) by 1679 days.

(21) Appl. No.: 11/321,057

(22) Filed: Dec. 30, 2005

(65) Prior Publication Data

US 2006/0195072 A1   Aug. 31, 2006

Related U.S. Application Data

(60) Provisional application No. 60/640,092, filed on Dec. 30, 2004.

(51) Int. Cl.
*A61B 18/18* (2006.01)
(52) U.S. Cl. ............... 606/10; 606/9; 606/13; 607/89
(58) Field of Classification Search ............... 606/2, 5, 606/10, 4, 9
See application file for complete search history.

(56) References Cited

U.S. PATENT DOCUMENTS

| | | | |
|---|---|---|---|
| 5,656,186 A | 8/1997 | Mourou et al. | |
| 5,720,894 A | 2/1998 | Neev et al. | 216/65 |
| 5,782,822 A * | 7/1998 | Telfair et al. | 606/5 |
| RE37,504 E | 1/2002 | Lin | 606/5 |

(Continued)

FOREIGN PATENT DOCUMENTS

| | | |
|---|---|---|
| EP | 0 502 101 | 12/1990 |
| EP | 0 589 468 | 3/1994 |

OTHER PUBLICATIONS

A. Vogel and V. Venugopalan. "Mechanisms of pulsed laser ablation of biological tissues.", *Chemical Reviews* 103.2 (2003) 577-644.

(Continued)

*Primary Examiner* — Sam Yao
*Assistant Examiner* — Lynsey Crandall
(74) *Attorney, Agent, or Firm* — Lynn C. Schumacher; Hill & Schumacher

(57) ABSTRACT

The present invention provides a method of laser processing of materials, specifically laser induced ablation processes for laser removal of material particularly important in medical and dental applications in which the laser removal of material should be done in such a way as to not damage any of the surrounding soft or hard biomaterial. The ablation process is achieved by impulsive heat deposition (IHD) by direct and specific excitation of short lived vibrations or phonons of the material in such a way as to not generate highly reactive and damaging ions through multiphoton absorption. The heat deposition and ensuing ablation process under prescribed time and wavelength conditions for laser irradiation is achieved faster than heat transfer to surrounding tissue by either acoustic or thermal expansion or thermal diffusion that otherwise would lead to excess heat related damage. The result is that all the deposited laser energy is optimally channelled into the ablation process in which the inertially confined stresses from both photomechanical expansion forces and thermally driven phase transitions and associated volume changes constructively interfere to drive the most efficient ablation process possible with minimal damage to surrounding areas by either ionizing radiation or heat effects. By choosing a specific range of wavelengths, spatial and temporal shaping of infrared laser pulses, the energy can be optimally deposited in a manner that further increases the efficiency of the ablation process with respect to minimizing collateral damage.

41 Claims, 10 Drawing Sheets

U.S. PATENT DOCUMENTS

| | | | | |
|---|---|---|---|---|
| RE37,585 | E | 3/2002 | Mourou et al. | 219/121.69 |
| 6,552,301 | B2 | 4/2003 | Herman et al. | 219/121.71 |
| 6,621,040 | B1 * | 9/2003 | Perry et al. | 219/121.67 |
| 6,824,541 | B2 * | 11/2004 | Boutoussov et al. | 606/5 |
| 6,943,964 | B1 * | 9/2005 | Zhang et al. | 359/708 |
| 2002/0016587 | A1 * | 2/2002 | Furumoto | 606/7 |
| 2004/0005349 | A1 * | 1/2004 | Neev | 424/443 |
| 2004/0195221 | A1 | 10/2004 | Haglund, Jr. et al. | |
| 2006/0195072 | A1 * | 8/2006 | Miller | 606/2 |

OTHER PUBLICATIONS

F. H. Loesel, M.H. Niemz, J.F. Billie, T. Juhasz. "Laser-induced optical breakdown on hard and soft tissues and its dependence on th pulse duration: Experiment and model." *IEEE J. Quant. Elect.* 32.10 (1996) 1717-22.

L. Genberg, Q. Bao, S. Gracewske, and R.J.D. Miller, "Picosecond Transient Thermal Phase Grating Spectroscopy—A New Approach to the Study of Vibrational-Energy Relaxation Processes in Proteins," Chem. Phys. 131 (1989) 81.

B. Rethfeld, K. Sokolowski-Tinten and D. von der Linde :Ultrafast Thermal Melting of Laser-Excited Solids by Homogeneouse Nucleation, Phys. Rev. B 65.9 (2002) 092103.

E. Leveugle, D.S. Ivanov, and L.V. Zhigilei, "Photomechanical Spallation of Molecular and Metal Targets: Molecular Dynamics Study", Appl. Phys. A 79, (2004) 1643.

G. Edwards et al., "Tissue ablation by a free-electron laser tuned to the amide II band," Nature 371 (1994) 416.

Laser-induced breakdown and damage in bulk transparent materials induced by tighty focused femtosecond laser pulses, Schaffer et al, Measurement and Science Technology, 12(2001) 1784-1794 Oct. 9, 2001.

A study of the deterministic character of optical damage by femtosecond laser pulses and applications to nanomachining, Joglekar et al, Applied Physics B77,25-30, Jul. 30, 2003.

Ultraviolet diffraction limited nanosurgery of live biological tissues, Colombelli et al, Review of Scientific Instruments vol. 75, No. 2, p. 472-478, Feb. 2004.

Breaddown threshold and localized electron density in water induced by ultrashort lase pulses, Fan et al, Journal of Applied Physics, vol. 91, No. 4, Feb. 15, 2002 p. 2530-2536.

Femtosecond laser ablation ICP-MS, Russo et al, j. Anal. At. Spectrom, 2002, 17, 1072-1075.

Frequency dependence of the ablation of pig tissue with an IR-FEL: a microspectroscopic analysis, Glotin et a, SPIE vol. 3775 Jul. 1999, 113-117.

* cited by examiner

Absorption Spectrum

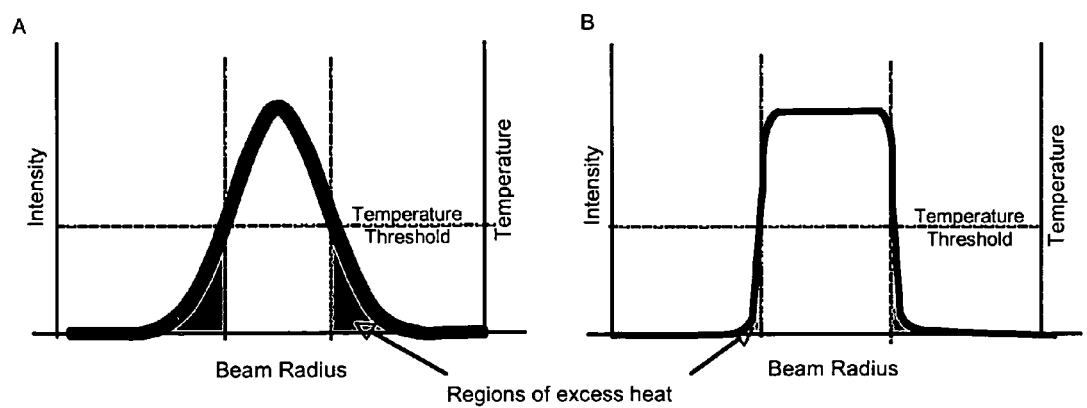
Figure 11A                    Figure 11B

LASER SELECTIVE CUTTING BY IMPULSIVE HEAT DEPOSITION IN THE IR WAVELENGTH RANGE FOR DIRECT-DRIVE ABLATION

CROSS REFERENCE TO RELATED U.S. PATENT APPLICATION

This patent application relates to U.S. provisional patent application Ser. No. 60/640,092 filed on Dec. 30, 2004 entitled LASER SELECTIVE CUTTING BY WAVELENGTH AND TEMPORAL TUNING IR PULSES TO PROVIDE MOLECULAR LEVEL OPTIMIZATION OF IMPULSIVE HEAT DEPOSITION PROFILES FOR ABLATION, filed in English, which is incorporated herein by reference in its entirety.

FIELD OF THE INVENTION

The present invention relates to a method of material removal using pulsed lasers. Impulsive heat deposition (IHD) through direct excitation of mechanical degrees of freedom (short lived vibrations or phonons) of the target material provides a novel ablation process that leads to a minimum of damage to the surrounding material. This low collateral damage is particularly advantageous in medical and dental applications in which the laser removal of material is preferably done in such a way as to not damage any of the surrounding soft or hard biomaterial.

BACKGROUND OF THE INVENTION

The ideal surgical tool would be as non-invasive as possible, by making the smallest cuts and removing the least amount of material possible. Since the invention of the laser, people have envisioned the use of laser based scalpels that are capable of removing or cutting away tissue with sub-micron accuracy. However, the problem to date with methods of laser surgery has been the deleterious collateral damage to surrounding tissue, which has limited the widespread use of lasers as a replacement for mechanical surgical tools.

Material ablation requires that the energy delivered by a laser to a material results in the irradiated volume of the material gaining sufficient translational energy to cause it to be removed. A number of mechanisms have been utilized, including "phase explosion" [1,2] and photomechanical spallation [1,3,4]. In the case of photomechanical spallation, the energy deposited must not exceed the vaporization threshold, and must be deposited quickly enough that shockwaves due to sudden thermal expansion lead to mechanical breakdown and ejection of the material. However, photomechanical spallation is notoriously inefficient, and it has been found that " . . . for most tissues, material removal using IR laser pulses cannot be achieved via a laser-induced spallation mechanism." [1]

In the case of "phase explosion", enough energy must be deposited to superheat the irradiated volume above the vaporization temperature of the material, leading to homogeneous nucleation and ejection of the material. The faster the heat is delivered to the material the faster the ablation process and the less amount of energy is lost by heat transfer to the surrounding material. Thus the degree of collateral damage depends strongly on the laser pulse width [1,5]. For long laser pulses (defined here as greater than 10 ns), there is significant heat transfer to the surrounding material. In the case of biological materials, the temperature gets so hot that the material actually burns. This latter process not only damages the surrounding tissue but actually blocks healing.

This dramatic effect is shown in FIG. 1, in which long pulses from conventional lasers are compared to short pulse ablation mechanisms in cutting bone as will be discussed below. Water cooling in combination with long laser pulses can help prevent the charring effect by excluding oxygen that is required for combustion. However, the material must still get hot enough to ablate in the irradiate volume and the excess heat which accumulates in the surrounding material leads to the tissue damage is the same. Excess heating of this magnitude still severely harms the adjacent tissue and thus has prevented the general use of conventional long pulse lasers in medical surgery.

It should be further noted that the time scale for heat deposition depends on both the time it takes for the absorbed laser energy (photons) to be converted to heat and the pulse duration of the incident light. The rate of lattice heating is a convolution of these two effects. The longer it takes the incident laser energy to be converted to heat the more time thermal diffusion and thermal expansion have to transfer energy to surrounding material and increase collateral damage. In the case of short laser pulses, it is possible to deposit the laser energy much faster than the ablation process, but realization of this is complicated by other deleterious effects as discussed below.

The threshold for ablation depends strongly on the energy deposited per unit volume. For a given amount of laser energy, the smaller the amount of material absorbing the light, the higher the temperature of the lattice rises in the irradiated zone, and the less total heat is available for transport to adjacent material to cause heat induced damage. In other words, the smaller the optical penetration depth, the less energy is required to achieve a particular temperature for ablation and the less total heat transferred to the material. The objective in minimizing collateral damage in laser cutting is to maximize the energy absorbed per unit volume or mass to increase the ablation efficiency.

To ensure a short absorption depth, excimer (UV) lasers can be used because all materials strongly absorb light in the UV to VUV wavelength range (here defined as micron to sub-micron absorption depths). However, this wavelength range leads to radiation damage by UV photochemistry and ionization of the material. This photochemistry is undesired in many applications and is a particularly serious problem in most medical and dental applications where ionizing effects and collateral photochemistry must be avoided in order to promote healing.

The alternative to the use of UV lasers is to use femtosecond (fs) laser pulses. With short enough pulses, it is possible to achieve high enough peak powers to drive multiphoton absorption processes that lead to strong absorption within the laser focal volume, even at wavelengths where the material is nominally transparent. However, the peak power must be raised to a level that leads to the ionization of the material's constituent atoms or molecules. The liberated electrons absorb light at all wavelengths and rapidly convert this energy to heat through a process referred to as avalanche ionization [6,7]. At high enough densities, the electrons and parent ions form a plasma that can further increase the absorptivity and further localize the heat deposition. In this short pulse limit, there is also rapid heat deposition. However, this process creates highly reactive intermediates. For solid state materials such as metals, this ionization process has no consequence as the ions are quickly discharged. In the case of biological materials, the presence of ions creates the same effect as highly ionizing x-ray radiation. Even in the absence of excessive heating in this short pulse limit of femtosecond durations, the effect of ion formation leads to damage that blocks healing and is unacceptable for most medical applications.

This problem has been identified by control studies of live animals in which it was found that even though femtosecond laser pulses cut without excess heating, the healing process was not invoked. There was sufficient damage to adjacent cells to kill them but not enough to trigger normal healing mechanisms. A signalling protein had to be used to induce healing as disclosed in co-pending U.S. patent application Ser. No. 60/704,905 filed Aug. 3, 2005 entitled "Hybrid ultrafast laser surgery-growth factor stimulation for ultraprecision surgery with healing". Note the effect of ionizing radiation from multiphoton absorption may also be significant in other non-biological materials. In the case of sensitive materials such as semiconductors, insulators, catalysts, etc., the ion induced chemistry will also lead to highly undesirable changes in material properties, such as the creation of surface states/defects. This effect again is most undesirable in any kind of medical or dental application. In the case of dental applications, the formation of highly reactive ions will have the potential for forming organic mercuric compounds from ablation of amalgam fillings that are incredibly toxic.

Another alternative is to tune the laser wavelength to maximize the energy localization into short lived excited states, such as vibrational transitions in the mid-infrared (mid-IR) wavelength range. Strongly absorbing vibrational modes, with micron to sub-micron absorption depths, can be found in biological and most other materials. By targeting these short-lived excited states thermal energy can be quickly transferred to a small irradiated volume, without the deleterious effects of ion generation and photochemistry. However care must be taken in the choice of both pulse duration and energy in order to achieve efficient, collateral damage free ablation.

SUMMARY OF THE INVENTION

This invention provides a method of laser processing of materials that is based on a new understanding of the ablation process and the dynamics of energy transduction of vibrational energy into heat. The invention disclosed herein provides a new methodology in which one can efficiently achieve material ablation with the minimum of collateral damage through either ion formation or thermal accumulation. This is accomplished by impulsive heat deposition (IHD), a novel method that combines both thermally and photomechanically driven ablation mechanisms, in-which most of the absorbed energy remains in the ablated material. The laser energy is effectively coupled directly to the mechanical degrees of freedom that lead to ablation and in so doing performs this task at optimal efficiency, which is key to minimizing collateral damage.

In one aspect of the invention there is provided a method of laser processing of a material, comprising the steps of:
irradiating a volume of a material with a pulsed laser beam in which the laser pulses have
  i) an energy sufficient that the light that is absorbed in the laser irradiated volume produces superheated temperatures above a vaporization point of at least one component of material contained in the laser irradiated volume,
  ii) a pulse duration time and wavelength that meets requirements for impulsive heat deposition such that the pulse duration time is shorter than a time required for thermal diffusion out of the laser irradiated volume and shorter than a time required for a thermally driven expansion of the laser irradiated volume, and
  iii) the pulse duration time is long enough and the pulse energy low enough so that a peak intensity of said laser pulses is below a threshold for ionization to occur in the material,
such that most of the energy contained in said laser pulses will be converted to ablation of the material in the laser irradiated volume with any residual energy not being enough to substantially damage material surrounding the laser irradiated volume.

In another aspect of the present invention there is provided a method of laser surgery on tissue, comprising:
irradiating a volume of tissue with a pulsed laser beam in which the laser pulses have
  i) an energy sufficient that the light that is absorbed in the laser irradiated volume of tissue produces superheated temperatures above a vaporization point of at least one component of tissue contained in the laser irradiated volume of tissue,
  ii) a pulse duration time and wavelength that meets requirements for impulsive heat deposition such that the pulse duration time is shorter than a time required for thermal diffusion out of the laser irradiated volume of tissue and shorter than a time required for a thermally driven expansion of the laser irradiated volume of tissue, and
  iii) the pulse duration time is long enough and the pulse energy low enough so that a peak intensity of said laser pulses is below a threshold for ionization to occur in the tissue,
such that most of the energy contained in said laser pulses will be converted to ablation of tissue in the laser irradiated volume of tissue with any residual energy not being enough to substantially damage tissue surrounding the laser irradiated volume of tissue.

The present invention also provides an apparatus for laser processing a material, comprising:
a laser source for generating laser pulses with wavelengths lying between about 1.5 and about 20 microns, and said laser pulses having
  i) an energy sufficient that the light that is absorbed in the laser irradiated volume of material produces superheated temperatures above a vaporization point of at least one component of tissue contained in the laser irradiated volume of material,
  ii) a pulse duration time and wavelength that meets requirements for impulsive heat deposition such that the pulse duration time is shorter than a time required for thermal diffusion out of the laser irradiated volume of material and shorter than a time required for a thermally driven expansion of the laser irradiated volume of material, and
  iii) the pulse duration time is long enough and the pulse energy low enough so that a peak intensity of said laser pulses is below a threshold for ionization to occur in the material,
such that most of the energy contained in said laser pulses will be converted to ablation of material in the laser irradiated volume of tissue with any residual energy not being enough to substantially damage tissue surrounding the laser irradiated volume of material.

BRIEF DESCRIPTION OF THE DRAWINGS

The method of laser surgery according to the present invention will now be described, by way of example only, reference being made to the accompanying drawings, in which.

FIG. 2A shows femtosecond laser ablation using 120 fs, 100 microjoule (µJ) pulses at 1 J/cm$^2$ fluence using a laser pulse that is spatially Gaussian;

FIG. 2B shows laser ablation using 100 ps laser pulses tuned specifically to the absorption of the OH stretch of water at 3,400 cm$^{-1}$ (2.8 µm) at a focused fluence of 1 J/cm$^2$ (left, Human dentin, pulse energy: 100 µJ, 1/e$^2$ beam spot size: 150 µm, cavity diameter: 45 µm, cavity depth 7 µm. Right pig jaw bone, pulse energy: 90 µJ, 1/e$^2$ beam spot size: 150 µm, cavity diameter: 40 µm, cavity depth 5 µm);

FIG. 2C shows a large 20 µm chunk of collagen fibre bundles ejected intact using the same conditions as in FIG. 2B;

FIG. 2D shows mouse skull bone, pulse energy: 90 µJ, 1/e$^2$ beam spot size: 150 µm, even more evidence for intact fibres are clearly seen;

FIG. 11A shows a temperature profile of a Gaussian pulse in which the temperature threshold for ablation is schematically shown wherein material that absorbs outside this temperature profile will not ablate but would experience excess heating; and FIG. 11B shows a square intensity profile or flat top laser pulse used to avoid excess heating by absorption in the wings of the pulse of FIG. 11B.

DETAILED DESCRIPTION OF THE INVENTION

Figure 1:
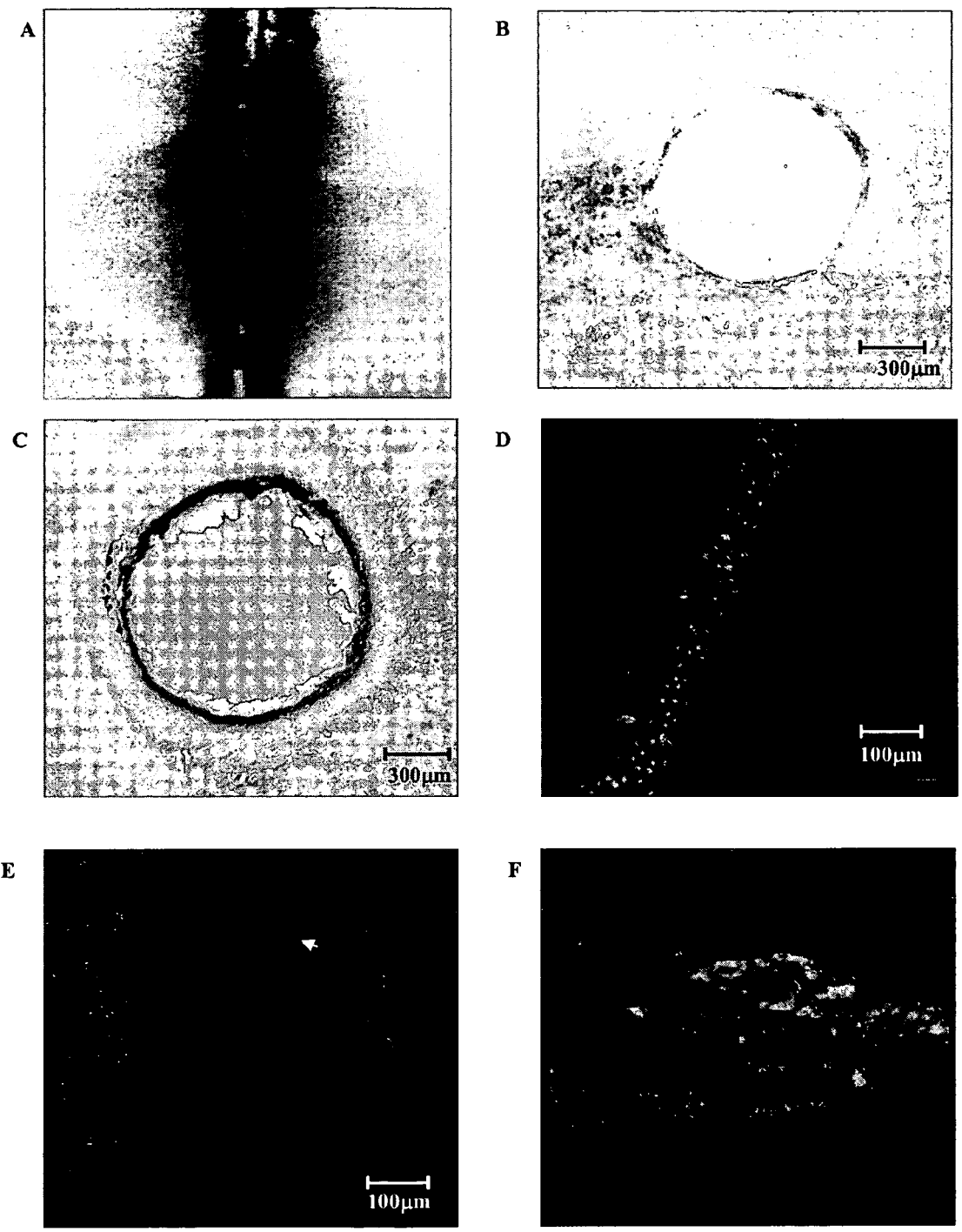
FIG. 1A shows a microphotograph of mice femur bone after laser irradiation with 532 nm pulses of pulse duration τ=150 ns duration, illustrating the extreme heat generated in biotissues with conventional lasers, which causes delayed healing and charring.
FIG. 1B shows a microphotograph of excised mice calvaria after laser irradiation with λ=775 nm 100 µJ/pulse, 1 kHz, τ=200 fs, Alkaline phosphatase (AP) staining of calvaria. AP (blue colour) is active on the cell surface in the area immediately adjacent to ablation.
FIG. 1C shows a microphotograph of excised mice calvaria after laser irradiation with λ=535 nm 1 mJ/pulse, 1 kHz, τ=150 ns, this micrograph clearly shows charring in the wound periphery, AP has been denatured up to 200 µm from the ablated area, indicating a temperature rise above 56° C. The brown circular area is charred tissue.
FIG. 1D shows a laser confocal image of tissue corresponding to FIG. 1B stained for intracellular enzymatic activity showing cell damage for approximately 2 cell layers thick.
FIG. 1E shows a corresponding cut in FIG. 1C showing cell membrane damage for upwards of 300 µm in thickness.
FIG. 1F shows a high power confocal image of the inside cut edge of 1B where cell-like shapes are still distinguished. This could not be replicated for ns cut because of the charred tissue.

The present invention describes a novel ablation approach that is based on new understandings of the ablation process and the dynamics of the transduction of vibrational energy into heat. The use of short laser pulses to optimally excite vibrations (or lattice phonons) and impulsively put energy directly into mechanical degrees of freedom enables a direct-drive mechanism for ablation. In so doing, this mechanism avoids the need for intermediate states and high peak powers that lead to deleterious side processes. The energy is wholly localized in mechanical degrees of freedom coupled to the ablation process. The invention disclosed herein provides a new methodology in which one can accomplish the same target state of superheating to drive ablation as with femtosecond pulse multi-photon absorption, but without the creation of ions in the process. The net effect is to have thermally and photomechanically driven ablation processes in which most of the absorbed energy goes into the ablation mechanism.

Using the method of impulsive heat deposition (IHD) that is disclosed herein, it is possible to achieve an ablation process with a minimum of collateral damage by depositing the energy directly into heat through a combination of short lived vibrational modes and strong localization of the absorbed light. If the energy can be converted to heat and create superheated lattice temperatures above the vaporization point of the material, most of the energy will be converted to ablation [12, 13].

The physics of the ablation mechanism with rapid heating involves an instability in which there is a phase transition from either solid or liquid to gas phase within the material as in a homogeneous nucleation process. Effectively the superheated material creates gas phase zones or voids in the material that create stresses that in turn couple to the stresses of thermal expansion that lead to material ablation. The intensity of the ensuing strain fields that develop in the material in response to these stresses is related to the energy channelled into ablation and this scales as the amplitude of the strain field squared which makes this constructive interference effect quite significant. These conditions lead to the most efficient transfer of the deposited energy into ablation, i.e. this process leaves the surrounding material as cold as possible after the ablation step. In the case of femtosecond laser pulse excitation, the energy driving the ablation is deposited into the electrons through multiphoton absorption and creation of free electrons and ionized matter.

These highly excited electrons deposit heat and create even more hot electrons through collisions with the lattice phonons in a process known as avalanche ionization [5, 7]. This ionization step needs to be avoided at all costs in many applications, as such ions are highly reactive.

These photoinduced hot ions may be acceptable in the ablation of hard metallic surfaces, but wreak havoc on biological systems and highly functionalized materials such as semiconductor devices. This effect is shown in FIG. 1D where a layer of damaged cells was induced by such effects. Heat can be deposited by other means to create the proper conditions for IHD. During the course of our work on water, we discovered that liquid water has incredibly short lived vibrational states [16] that deposit energy directly into librational motions or heat. This process actually occurs faster (in 30 to 200 fs) than the time scales for electrons to pump energy into lattice phonons or heat [17] as occurs in femtosecond laser pulse driven electron avalanche mechanisms.

Remarkably, this relaxation of energy occurs on the same time scale as the librational motions themselves. The IHD process is identical to exciting the librations or depositing the energy directly as heat. These observations on fast vibrational energy relaxation and the background studies on femtosecond ablation led to the realization that a new mechanism for energizing materials could be introduced to avoid the effects of ionizing radiation. By tuning the laser wavelength to maximize the energy localization into short lived vibrationally excited states, IHD can be driven without the ion or plasma formation that occurs when using ultrashort pulses (ultrashort defined here as less than 1 ps).

The other key physical information is that for fully resonant conditions, the IR absorption into specific vibrations is extremely strong and provides a natural means to localize the energy in a molecularly selective way. The vibrational modes of water (OH stretch, OH bend and combinations) are specifically very useful for laser cutting of biological materials. The lifetime of these vibrations are less than 200 fs so the laser deposited energy will essentially track the laser pulse time profile. In addition, the absorption is so strong that 90% of the IR tuned to the OH vibration is absorbed in less than 1 µm. However, many other molecular vibrations are sufficiently short lived to satisfy the condition of IHD in relation to thermal and acoustic transport out of the energized zone. Most materials have a sufficiently high number density of at least one vibrational mode in a material, to ensure strong localization of the laser deposited energy.

The strong localization of light energy into short lived vibrational modes that couple directly to heat without ion formation on a sufficiently short time scale is the key enabling concept. This concept also enables a high degree of selectivity by tuning the laser wavelengths to match the target material, even to the point of molecular selectivity. This molecular selectivity by wavelength tuning of the laser is particularly advantageous when trying to remove a single specific material from a target. Important applications include removing tumour cells that have specific spectral markers or only removing dental caries selectively from good tooth matrix. These are just two important examples.

The method disclosed herein involves the use of a laser pulse that is shorter in duration than both the thermal diffusion time out of the laser irradiated area and more restrictively, the time for thermally driven expansion. The times for thermal diffusion and thermal expansion must be defined in the context of the length scale of the observation. In the case of thermal diffusion, the important dimension is typically the laser spot size or cross sectional area. One is usually drilling down in direction as each laser shot only removes between 0.1 to 1 µm of material (material and wavelength dependent). Assuming that typical laser parameters will involve laser spot sizes between 10 to 100 µm, to minimize the volume of excited material yet provide a reasonable working distance for the focusing optics, the thermal diffusion time in the lateral direction will be generally longer than 1 microsecond. With the above stated condition of strong localization of the absorbed light, thermal diffusion is faster in the longitudinal direction (normal to the surface). In this direction, the light absorption ideally will occur within 0.1 to 1 µm from the surface. The thermal diffusion time in this case can be on the order of 10-100 ns depending on the material's thermal diffusivity.

However, beyond the thermal transport limits, the more stringent requirement is for the pulse to deliver energy faster than thermally driven expansion. This process occurs at the speed of sound and not through a process of diffusive collisional exchange. Now in this case, the quickest cooling process is the thermal expansion in the longitudinal direction. For micron deep irradiated volume, the thermally driven sound fields attain maximum amplitude at times less than it takes the speed of sound to propagate across the absorption depth of the light. This time defines the IHD limit. For speeds of sound typical of most condensed matter (between $10^5$ to $5 \times 10^5$ cm/s) this time scale is between 200 ps and 1 ns for 1 µm heated zones. For materials that have higher absorption, such as metals, the light absorption can be localized in a depth as short as 0.1 µm, this time scale reduces to 20 to 100 ps. Ideally the pulse duration should be somewhat shorter than this time to minimize the loss of absorbed energy into the surrounding material by acoustic transfer. For IHD, the pulse duration should be shorter than the acoustic expansion time, thus for most materials the required pulse duration lies between 10 ps to 1 ns.

The above prescription describes how to determine the pulse durations that are required for optimal IHD. This prescription is perfectly suited to the use of IR light that is tuned to molecule specific/material specific vibrations. The vibrational lifetime is almost universally shorter than 10 ps [18, 19], so the energy deposited will effectively be converted directly to heat within the pulse duration.

For biological materials in which the energy is localized to 1 µm depths, and the speed of sound is closer to that of water ($2 \times 10^5$ cm/sec), pulses on the order of 100 ps will be close to optimal. Shorter pulses have higher peak power, and thus it needs to be stressed that there is a lower limit to the pulse duration set by the intensity threshold for ionization of the material.

Figure 2:
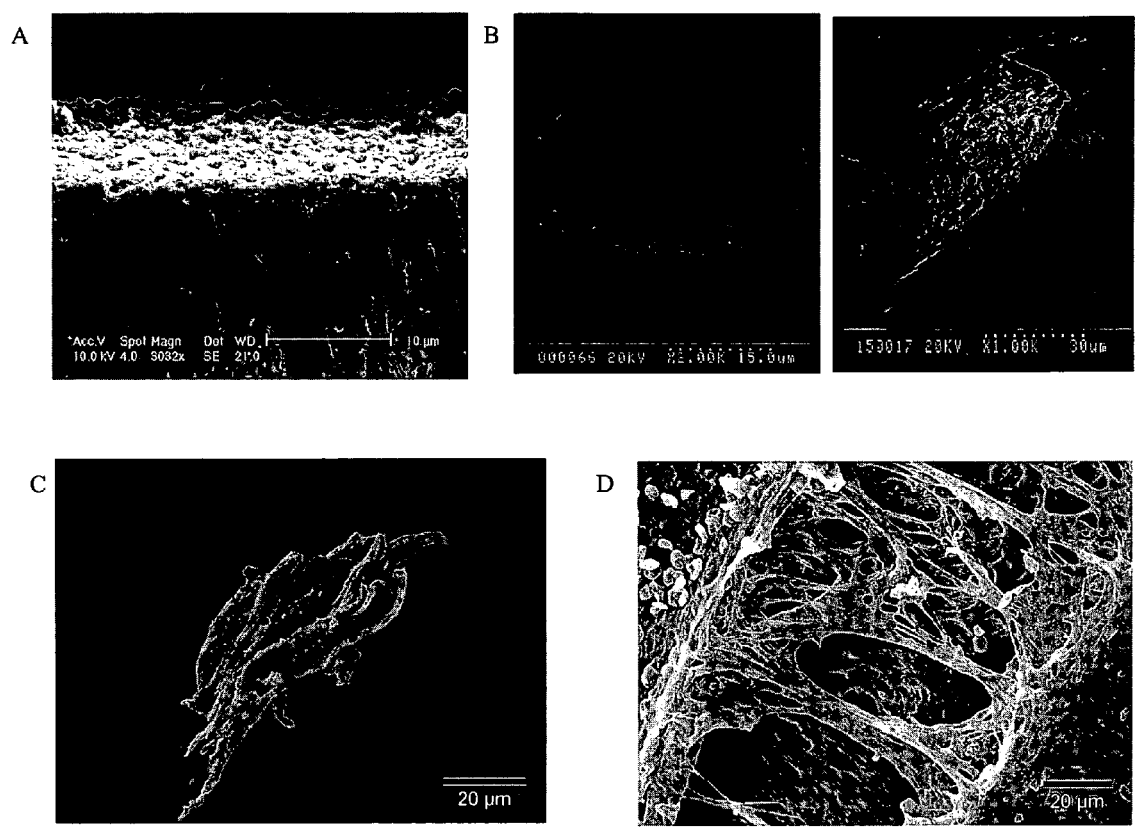
FIGS. 2A to 2D show a direct comparison of laser ablation using femtosecond laser pulses and short pulse IR ablation with bone as the substrate.

FIGS. 1 and 2 show the dramatic differences between ablation from ultrashort laser pulse in the femtosecond domain, conventional long pulse lasers of 1 ns or longer, and that of the IHD by short IR pulse (short pulse defined here as 1 ps to 1 ns) of this invention. The differences clearly illustrate the advantages of short IR pulses in the prescribed pulse duration range for direct energy deposition and strong localization of the energy.

More particularly, FIGS. 1A to 1E show the effects of laser ablation using short pulses and long pulses with bone as the substrate. FIG. 1A shows a microphotograph of rat femur bone after laser irradiation, illustrating the extreme heat generated in biotissues with conventional lasers, which causes delayed healing and charring. For the study of living bone tissue, we extended the studies to mice calvaria as shown in FIGS. 1B-F. These figures are included to highlight the importance of healing in the consideration of laser cutting of biological tissue for medical and dental applications. FIG. 1B shows microphotographs of excised mice calvaria after laser irradiation with λ=775 nm 100 μJ/pulse, 1 kHz, τ=200 fs, with alkaline phosphatase (AP) staining of calvaria. AP (blue colour) is active on the cell surface in the area immediately adjacent to ablation and FIG. 1B shows that the short pulse laser cutting leads to very clean cuts without charring. FIG. 1C shows a microphotograph of excised mice calvaria after laser irradiation with λ=535 nm 1 mJ/pulse, 1 kHz, τ=150 ns, this picture clearly shows charring in the wound periphery, AP has been denatured up to 200 μm from the ablated area, indicating a temperature rise above 56° C. The brown circular area is charred tissue. The results in FIG. 1C show the problems of ablating with long pulses, since heat has sufficient time to transfer to adjacent material outside the laser irradiated zone. The formation of significant carbonized zones clearly demonstrates that the temperature reached by the surrounding material was high enough to combust but insufficient for ablation. This charring precludes healing and is highly deleterious. This problem is not only specific to biological materials but to any material with a high degree of functionality (e.g. semiconductor devices).

FIG. 1D shows a laser confocal image of the same femtosecond laser cut as FIG. 1B, stained for intracellular enzymatic activity, which reveals a 2 cell thick damaged layer surrounding the cut. FIG. 1E (the same long pulse cut as FIG. 1C) shows cell membrane damage in a 300 μm thick layer surrounding the cut, and FIG. 1F shows a high power confocal image inside the cut edge of FIG. 1B where cell-like shapes are still distinguished. This could not be seen for the long pulse cut because of the charred tissue.

FIG. 2 shows a direct comparison of laser ablation using femtosecond laser pulses and IHD using short IR pulse ablation with bone as the target. The significant differences in the ablation structure clearly demonstrate the very different ablation mechanisms at play for the two processes. FIG. 2A shows femtosecond laser ablation using 120 fs, 100 μJ pulses at 1 J/cm² fluence. Note the very sharp edges, and smooth, flat profiles. The laser pulse itself is spatially Gaussian yet the sharp features arise from the high nonlinearity of multiphoton absorption, and subsequent saturation of absorption once a plasma forms [20].

The formation of plasma leads to massive ionization, fragmentation, and complete disintegration of the material, and thus very smooth surfaces. In contrast, FIG. 2B shows laser ablation using 100 ps laser pulses tuned specifically to the absorption of the OH stretch of water at 3,400 cm−1 (2.95 μm) at a focused fluence of 1 J/cm². Two different regions show the effect of heterogeneity. Note, the scanning electron micrograph on the right in this figure (2B) shows huge sections of intact collagen that look much like intact spaghetti being lifted by a fork. The depths of the ablation craters are 7 times larger than the femtosecond case, for the same fluence, which demonstrates the higher efficiency of IHD using vibrational modes. The most important observation is that the walls are no longer smooth. There are huge sections, many microns long, of intact collagen fibre ejected in the ablation step as evident most graphically in FIG. 2C. A large 20 μm chunk of collagen fibre bundles ejected intact is shown in FIG. 2C using the same ablation conditions as in FIG. 2B.

FIG. 2D shows mouse skull bone, with even more evidence for intact fibres clearly visible. Subsequent pulses near the periphery or repeated excitation of the same volume remove the residual material in the cutting process. The key observation is that rather than an extremely smooth surface as in the case of femtosecond cutting, enormously large molecules and fibres are ablated intact. This very significant difference is central to laser cutting with minimal damage, and subsequent improved healing of the cuts.

Since there is no laser gain material suitable for the generation of the sub-ns mid-IR pulses required for IHD, historically only free electron lasers have been able to reach this pulse regime with the necessary energy. However the ps pulses produced by free electron lasers are not suitable for IHD, since they are produced in packets of many ps pulses closely spaced in time forming a "macropulse" with a much longer duration than the impulsive limit as specified below. These free electron laser pulse packets lead to accumulated collateral damage [21] because the ablation process does not complete before the next pulse in the packet arrives at the sample, thus the effective duration of the pulse packet is that of its long integrated heating envelope and not its constituent picosecond pulses. Ultrafast mid-IR spectroscopy has been enabled by the use of non-linear parametric frequency mixing to transfer energy from conventional laser sources to mid-IR wavelengths. Generation of mid-IR sub-ns pulses of the required energy is now possible using optical parametric techniques. This new laser technology greatly simplifies the attainment of short IR pulses for true IHD over that of IR free electron lasers (FEL). It should be noted that IR FELs are large international research facilities. With the more efficient mechanism and relaxed pulse duration constraints of IHD relative to femtosecond laser processing of materials, low cost, compact, solid state lasers can now be used to realize laser cutting with minimal damage and is another advantageous feature of the present invention. Further details of a preferred laser source for use in doing the present invention is disclosed Applicants copending U.S. patent applications Ser. No. 10/129,649 filed May 16, 2005, published as US Patent Publication No. 20050271094, and U.S. Provisional Patent Application No. 60/642,113 filed on Jan. 10, 2005 and its corresponding full utility U.S. patent application Ser. No. XXX filed on Jan. 10, 2005, all of which are incorporated herein by reference.

Figure 3:
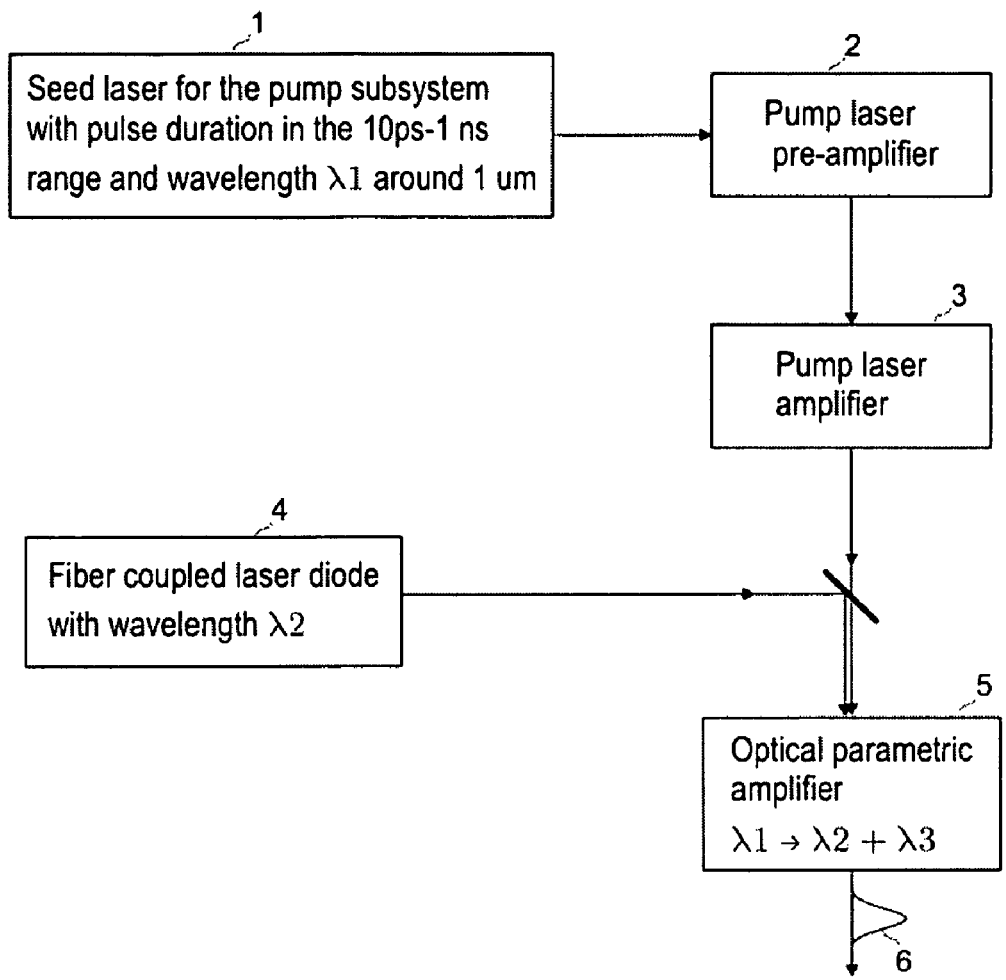
FIG. 3 shows a schematic layout of an infrared (IR) pulsed laser apparatus for laser surgery constructed in accordance with the present invention.

FIG. 3 shows one possible embodiment of a simple and compact source of sub-ns IR pulses for wavelengths from 1.5 -12 μm. The laser system includes a seed source laser 1 for the pump subsystem. It produces low energy pulses with wavelength λ1 around 1 μm. The laser system may include an optional pump subsystem preamplifier 2, which receives and amplifies pulses from seed source 1 which are then directed into pump subsystem amplifier 3. The system includes a fiber coupled laser diode 4 with wavelength λ2 tuned to the λ1-λ3 where λ3 is the wavelength of the targeted molecular vibrational transition. The system also includes an optical parametric amplifier 5, where the pulse with wavelength λ1 is used as a pump and the laser radiation (continuous or pulsed) with wavelength λ2 is used as a seed. The system produces an energetic pulse 6 with the desired wavelength λ3 and pulse duration 1 ps to 1 ns. We have demonstrated such a system with pulse energies >200 μJ and average powers of >200 mW. The pulse energy and repetition rate of such a system can be readily improved by a person skilled in the art.

Incorporating a method of pulse shaping into the tuneable sub-nanosecond infrared (IR) pulsed laser surgery apparatus allows creation of pulses or bursts of pulses with a time envelope τ<1 ns. Time and spectral shapes of these pulses are optimized for maximum heat deposition at the target while avoiding problems with multi-photon ionization and bleaching as described below.

Figure 4:
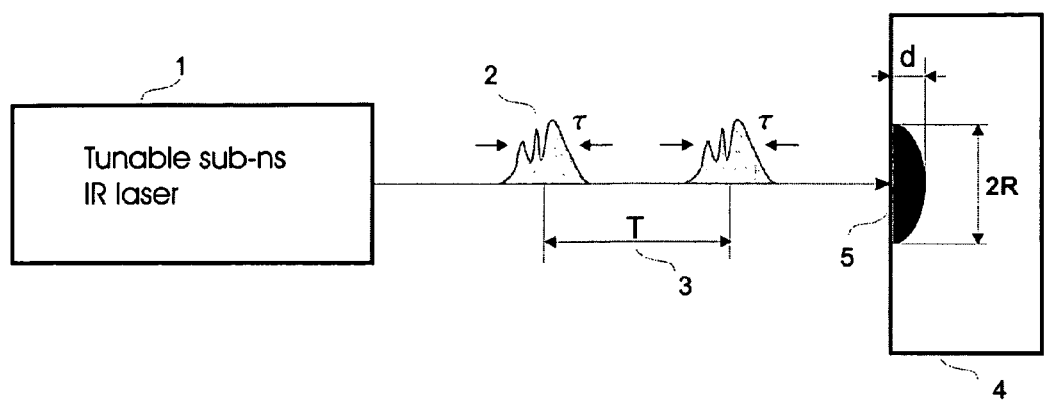
FIG. 4 shows the output of a tuneable sub-nanosecond IR pulsed laser surgery apparatus shown in FIG. 3 with incorporated pulse shaping, showing the a schematic of the shaped pulses incident on the irradiated volume.

For laser pulses directed at a region of material, the irradiated volume of the material has spatial properties which are determined by the laser beam parameters and the material properties. FIG. 4 shows the irradiated volume, 5, schematically. It has a radius, R, defined by the radius of the spatial intensity of the laser beam and a depth, d, define the absorption depth. For IHD to occur, the pulse envelope length τ should be shorter than the time that sound in the target material takes to travel across the longitudinal and transverse lengths of the affected zone 5.

$$\tau < d/v_{sound},$$

$$\tau < 2R/v_{sound},$$

where d is the 1/e absorption depth, $v_{sound}$ is the speed of sound of the target material, and R is the radius of the spatial intensity of the laser beam (FWHM). It should also be shorter than the thermal diffusion time from the affected zone in both longitudinal and transverse directions:

$$\tau < d^2/6D$$

$$\tau < (2R)^2/6D$$

where D is the thermal diffusion constant. For biological tissues $D \sim 10^{-7}$ m$^2$/s is typical. Pulses are emitted from the laser apparatus separated by a period, T, corresponding to the repetition rate. The time between pulses should be longer than thermal diffusion time from the affected volume 5

$$T > d^2/6D$$

$$T > (2R)^2/6D$$

of the target material. This condition is met to avoid the accumulation of residual heat between laser shots and the associated problems of heat damage. The depth d of the irradiated zone is on the order of $\alpha^{-1}$ as an effective absorption length where α is the absorptivity of the material at the wavelengths of the laser pulse. In order to have effective heat deposition this absorption length should be on the order of 1 μm. The transverse diameter 2R of the affected zone will generally be on the order of 10-100 μm for practical applications.

Figure 5:
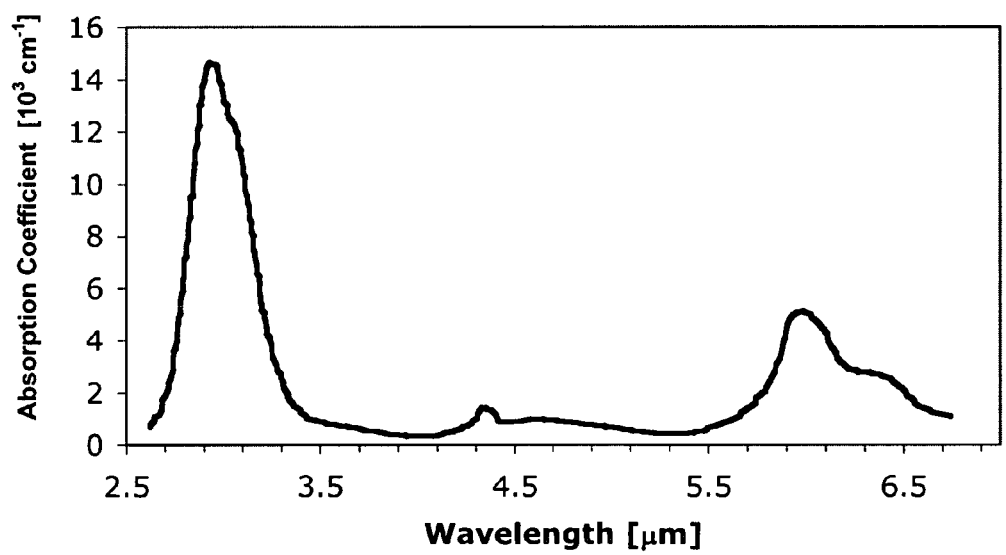
FIG. 5 shows the absorption coefficient as a function of wavelength between 2.5 and 7 µm for human corneal stroma, typical also for brain tissue, cartilage, and disc material, with comparably high water content; (from reference 15)

The vibrational absorption spectrum of biological tissue generally exhibits strong absorption at the OH vibrational modes of water. FIG. 5 shows the absorption coefficient as a function of wavelength between 2.5 and 7 μm for human corneal stroma, typical also for brain tissue, cartilage, and disc material, with comparably high water content. For biological materials, this invention covers the selective heat deposition into micropools of high water content in the irradiated volume, as a molecularly selective means to deposit energy into regions where the least amount of energy is required to drive the combined photomechanical and thermally derived phase change components of the IHD response, since water has the highest vapour pressure and lowest boiling point of the constituent materials of biological tissues. The phase change transfers the acoustic response to the remaining irradiated volume as the density in the water region decreases with the phase expansion. This process focuses the thermal energy into stresses, and leads to a much more efficient ablation process in heterogeneous biological materials. All of the deposited energy remains in the mechanical degrees of freedom needed to drive the ablation process with minimal transfer of energy to adjacent material and thus provides the minimum collateral damage.

Figure 6:
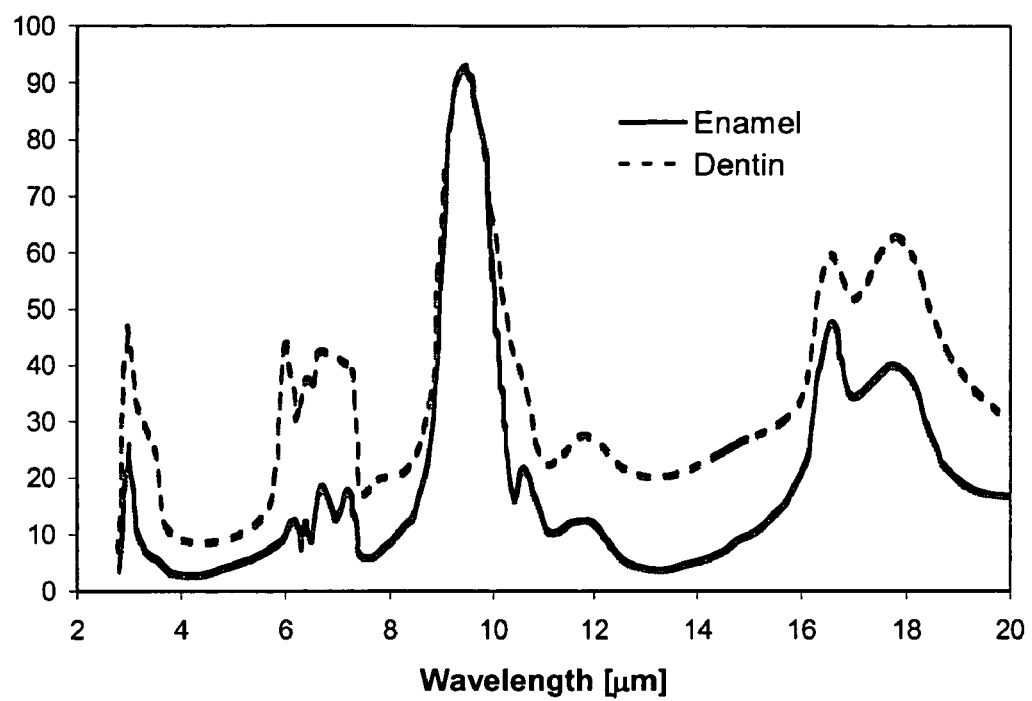
FIG. 6 shows the relative absorption of dentin and enamel in teeth between 2.5 and 20 µm; (from reference 15)

For these biological materials, the amide band of the protein also contributes strongly to the IR absorption and could be used to selectively cut protein rich material and avoid cutting other regions. FIG. 6 shows the relative absorption of dentin and enamel in teeth between 2.5 and 20 μm. Here water transitions still contribute but there are other very strong transitions that can also be used to selectively cut different parts of the tooth, depending on molecular composition.

Since most vibrational lifetimes are on the order of a few picoseconds to 10 ps, pulses shorter than this duration will lead to bleaching. This phenomena occurs in which the accepting state in the process of being excited is promoted to a new state that no longer absorbs in the same spectral region as the unexcited material. The material is said to bleach and thereby become more transparent. To attain the strongest localization of absorbed light this process should be avoided. Pulse conditions to deliver the energy need to be manipulated to avoid bleaching.

The optimal pulse duration in which a maximum of energy absorbed per unit volume or mass can be delivered without ionization and bleaching effects is determined by the material properties of the target, particularly the resonant absorption. It should be stressed that the pulse energies need to produce heat without leading directly to ion formation or excessive bleaching. Optimal pulse durations would scale linearly for greater absorption depths given a maximum intensity limit as defined by the ionization threshold through multiphoton absorption.

Figure 7:
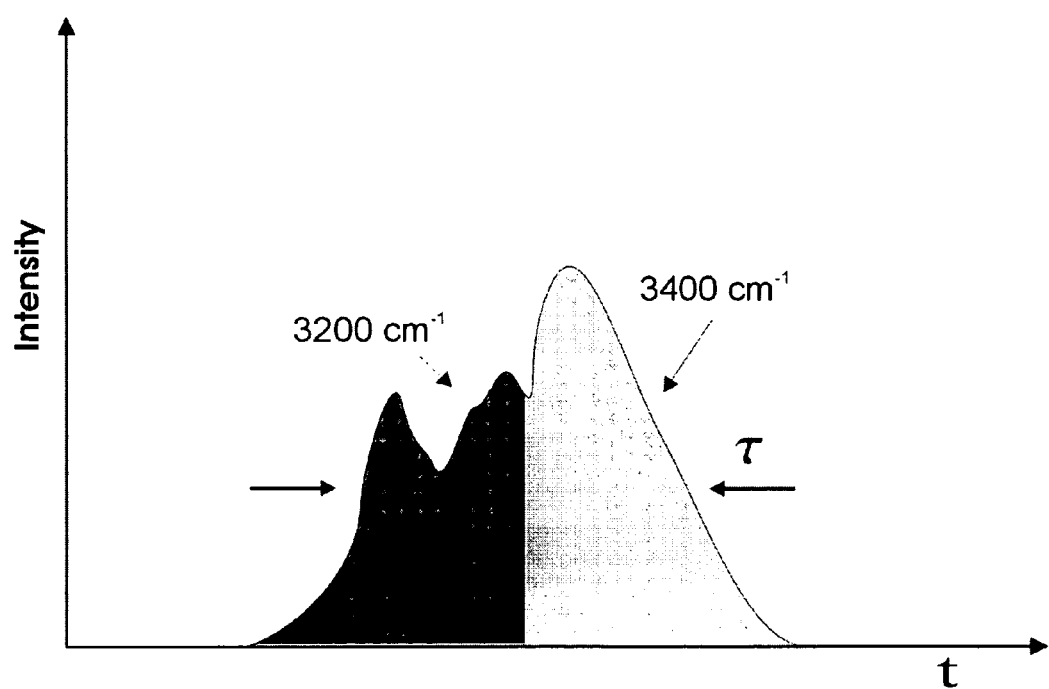
FIG. 7 shows a simple example of wavelength time multiplexing to avoid bleaching effects in which the front edge of the pulse has a wavelength (3400 cm$^{-1}$) tuned to the OH stretch vibration of water; the back edge (in time) of the pulse (dark area) is tuned to the excited state absorption at 3200 cm$^{-1}$. The pulse spectrum could also simultaneously include other frequencies tuned to other vibrations such as the OH bending mode at 1600 cm$^{-1}$

Furthermore, excited OH stretch modes will absorb strongly at a red shifted wavelength centered at 3200 cm$^{-1}$ due to the anharmonicity of the OH potential energy surface [16]. Thus, the simplest method to circumvent bleaching effects is time-wavelength multiplexing, as depicted in FIG. 7. In this method, the front edge of the pulse is chosen to have a wavelength tuned to the OH stretch vibration of water at 3400 cm$^{-1}$ and the trailing edge of the pulse is tuned to the excited state transition to keep the average absorption constant and localize the absorbed light energy in the smallest possible volume. Such temporal and wavelength profiles can be crafted from known laser pulse shaping technologies. This same prescription could be used combining other vibrational modes as well.

Figure 8:
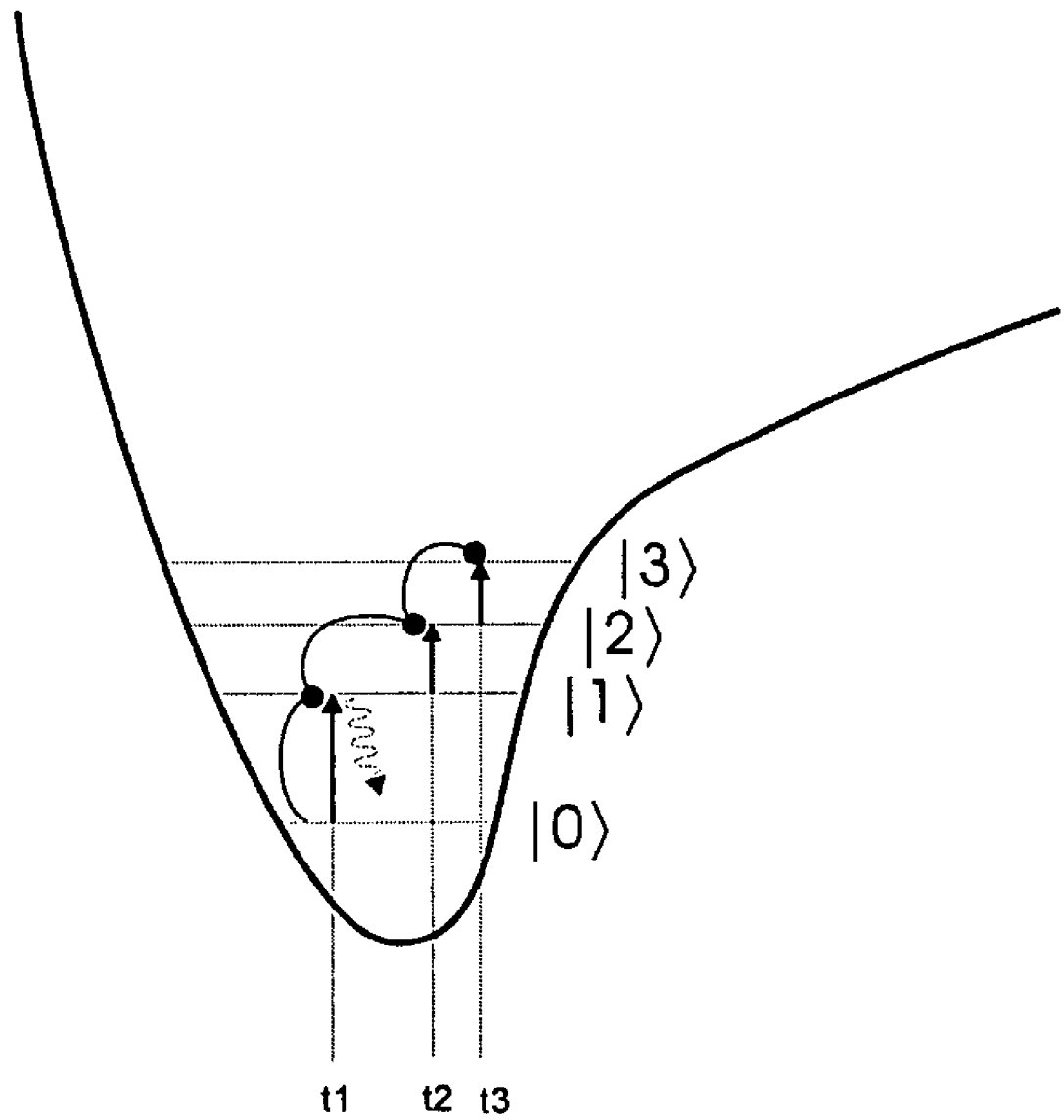
FIG. 8 shows a process of temporal pulse shaping to access excited state transitions wherein IR "ladder climbing" is shown as a means to increase the absorption of light.

Pulse shaping can be used to access many excited state transitions as a means to increase the absorption of light. For example, the effect of IR "ladder climbing" is shown schematically in FIG. 8. This can be achieved with pulse shapes that contain red shifted spectral components occurring later in time which can be absorbed by excited state transitions from levels which have already been populated by the pulse. The optimum pulse shape would not be discrete but rather a smoothly varying "chirp" in frequency to the red to drive this ladder climbing process dynamically to minimize the bleaching effects of the ground state. As the material is heated, the anharmonic coupling between modes leads to spectral changes and time-wavelength multiplexing can be equally employed to compensate for this effect to maximize the localization of the light absorption.

Figure 9:
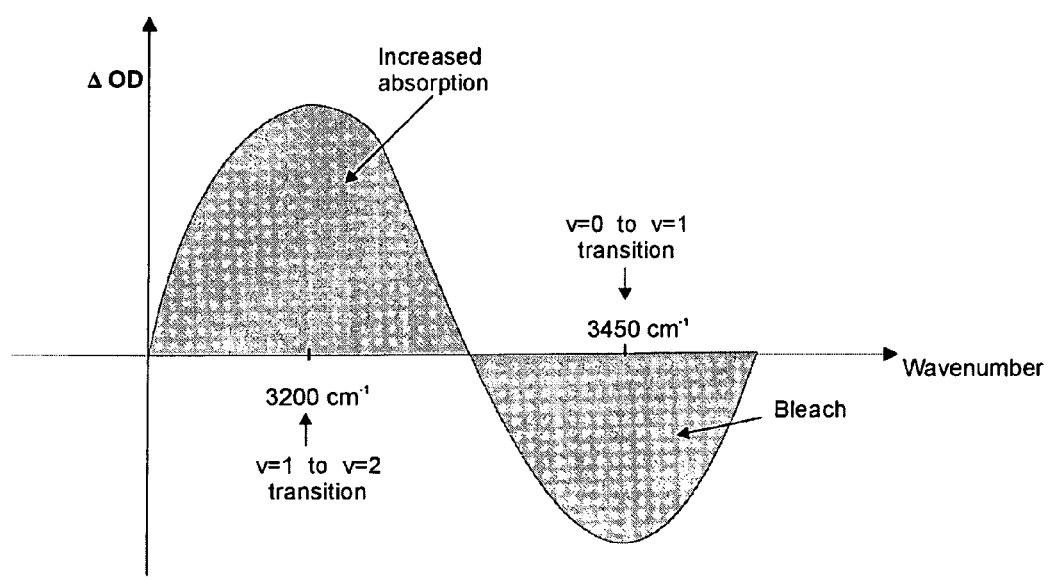
FIG. 9 shows a schematic of the anharmonic shift of the absorption of the OH-stretch of water during the excitation process.

Water is the most abundant substance and will likely be the primary target in most IR laser driven ablation processes in biological tissues. In water, the excited state frequency shift is approximately 200 cm$^{-1}$ as illustrated in FIG. 9. This value depends on the vibration and the surrounding medium and is only given as an example. Pulsed excitation at a single wavelength tuned to the ground state IR transition produces a decrease in absorption at the ground state frequency and an increase in the excited state absorption [16]. Thus, to avoid bleaching, the chirp or temporal-wavelength profile on the laser pulses needs to be tuned to the specific anharmonicity of the molecular modes, which can be determined independently using standard techniques.

Figure 10:
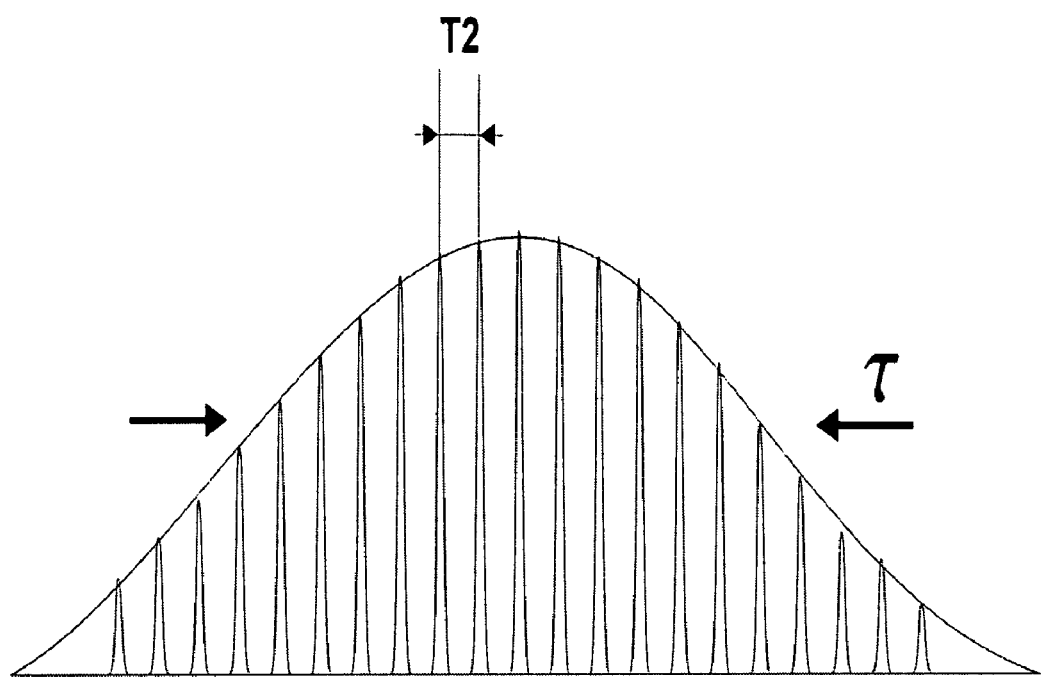
FIG. 10 shows another possible temporal shape of the IR laser energy bundles consisting of series of short IR pulses that have IR wavelengths chosen according the criteria mentioned in the text but instead of one <1 ns pulse there is a burst of laser pulses under the envelope with length T that satisfies the same conditions as before, i.e, it is smaller than the thermal diffusion time from the affected zone and smaller than the time that sound in the target material takes to travel across the transverse and longitudinal dimension of the affected zone.

FIG. 10 shows another possible temporal shape of the IR laser energy bundles. It consists of series of short IR pulses that have IR wavelengths chosen according the criteria disclosed herein but instead of one <1 ns pulse there is a burst of laser pulses under the envelope with length τ that satisfies the same conditions as before, i.e. the pulse envelope is shorter than both the thermal diffusion time from the affected zone and the time that sound in the target material takes to travel across the transverse and longitudinal dimension of the irradiated zone. Separation between pulses should be larger than the lifetime of the excited state of the vibrational transition which is the main absorber giving the excited vibration time to relax back to the ground state after the energy is deposited. In this way, problems with bleaching and multiphoton ionization become smaller. Combinations of the above shape, with closely spaced pulses, and additional wavelengths tuned to other strong IR transitions and/or dynamic compensation of spectral shifts can be used to further increase the localization of the absorbed light energy for high efficiency IHD ablation with minimal thermal transfer of energy outside the targeted zone.

The radial profile of the incident laser is also important in localizing the thermal transfer of energy. FIG. 11A shows the temperature profile of a Gaussian beam incident on a material. The ablation threshold is only exceeded by the central portion of the beam and the material that absorbs outside this portion will not ablate and could accumulate heat. The square intensity profile or flat top laser pulse shown in FIG. 11B is used to minimize this problem since it avoids heating caused by absorption in the wings of the pulse of FIG. 11B.

A significant aspect of the present invention disclosed herein is the use of laser wavelengths or combinations thereof that create excited states that have: 1) short lifetimes (shorter than the required pulse durations as defined above); 2) non-radiative relaxation and direct heat generation faster than the required time for the pulse durations; and 3) involve selective tuning of the laser radiation to the material properties by both peak power and wavelength to attain strong absorption conditions. This latter property of light can be manipulated to achieve molecular level control.

A preferred embodiment of this invention is the use of short infrared laser pulses (using the definition for short times above) that are tuned to vibrational modes of the material being processed. The laser radiation needs to be tuned to a particular vibrational mode that absorbs strongly enough for the absorbed energy and subsequent heating process to be localized in less than 100 microns and preferably in micron to sub-micron dimensions. This condition can be readily appreciated. If the energy is absorbed over longer dimensions, the pulse energy required to achieve the same heating rate will need to be increased. As the energy is increased for a given laser pulse duration, the peak power on the same surface area subsequently increases. This peak power should not exceed the threshold at which ions are created by multiphoton absorption. This statement further recognizes the limitations in energy per pulse for a given laser system for even high brightness lasers (TEM00) and the requirement that the least energy per pulse possible be absorbed to minimize collateral damage.

As a general rule, it is possible to find a strongly allowed vibrational transition in the infrared that leads to localization of absorption on micron to sub-micron dimensions. These vibrational states need to generate heat fast enough to satisfy the impulsive limit as defined above for superheating and ablation. For example, in biological tissues it is very straightforward to tune to the OH stretch of water that is a dominant component.

The absorption of the OH vibrational stretch is so strong that absorption occurs within 0.75 μm for aqueous environments. Furthermore, it has been determined by the inventor that the vibrational lifetime is on the order of 200 fs [16] and relaxes directly through coupling to low frequency motions of other surrounding waters. Simply put, the vibrational energy relaxed directly to heat. This relaxation mechanism actually deposits the absorbed laser radiation into heat faster than even femtosecond laser multiphoton excitation (the excited electrons need to still relax by relatively inefficient electron-phonon scattering) but with the key distinction that ions are not directly produced. The energy is effectively deposited directly into heat or translational degrees of freedom; the same degrees of freedom required to cause ablation. This mechanism of energy localization on sufficiently short time scales selectively couples the laser energy directly into the modes driving ablation for an effective direct-drive mechanism.

One can tune the laser radiation to other vibrational modes for the same effect. Almost all vibrational modes have lifetimes less than 10 ps and relax in a process that generates heat on this same timescale. The procedure is then to simply tune the laser radiation in the infrared spectral region to match the vibrational mode of interest. This vibrational mode would typically correspond to the dominant constituent of the material intended for removal. If the IR absorption is not sufficiently high for the desired effect, the light can be further localized in space by including multiple wavelengths or invoking energy delivery through multiple vibrational modes as heat sources to assist in IHD.

It is noted that there are several aspects of the inventions and ideas expounded that distinguish it as novel:

The invention is based on optimal absorption of light to create impulsive ablation conditions in the smallest volume element possible to create minimally invasive/damaging conditions for cutting.

The present invention solves the problem of collateral damage due to laser cutting. This problem is evident with long pulsed lasers using IR to UV wavelengths, which cause either excess heating, boil off, or gross material damage (fracture, cracking, stress lines). In the medical and dental area, long pulses have caused charring of tissue (barbeque effect) with large zones of carbonation sited. This effect is clearly demonstrated in FIG. 1. Charring of tissue leads to large zones of necrotized material with either no prospect for healing or very bad outcomes with significant scarring, far worse than any mechanical tool for the same function. Despite these limitations, there are patents for the use of IR wavelengths to cut materials. The most notable are the ones based on Er:YAG and other laser gain media that produce long pulses in the 2.9 μm wavelength range. U.S. Pat. Nos. 6,824,541 [14] and 5,782,822 [10] are directed to a method of corneal sculpting using a IR laser. These patents pertain to the use of Er:YAG and other lasers in the 2.9 μm range and specifically define pulse energies greater than 100 microjoules to do the cutting and involve much longer pulse durations than that imposed by the current invention as optimal for IHD. The energy range specified [14] is well above the minimal energy required for ablation using the new concepts described herein and illustrates that the IHD mechanism is not exploited or considered in these other patents involving the use of IR wavelengths [9, 10, 14] as elaborated above.

A key distinction is that prior art exploited laser pulses or combs of laser pulses of duration longer than 1 ns for both technical and conceptual reasons relating to the operative mechanism; whereas the concepts embodied in this patent are to use <1 ns pulses specifically use IHD for a direct drive cold ablation process as defined above. It is noteworthy in this respect that such laser approaches using long pulses in dentistry (>1 ns) require high pressure water jets to cool materials to avoid burning and even with such measures collateral damage occurs. In fact, the actual cutting mechanism is more related to superheating and induced cavitation in the applied cooling water than direct absorption in the tooth for dental applications. This latter point is clear as the absorption of water is so large that any external source of water applied to the tooth would absorb essentially all the laser energy before it could be deposited directly in the tooth. The present invention disclosed herein describes the wavelength and temporal tuning of IR lasers to produce optimal conditions for depositing the minimal energy into materials to cut with minimal collateral damage. The use of water under high flow conditions for cooling and other measures are not necessary with the present method.

One of the biggest problems cited with Er:YAG lasers in dentistry is the high water flow that obscures the vision of the dentist in performing the task. Furthermore, the use of high volume water streams for cooling necessitates larger working distances and therefore much higher pulse energies for the associated larger spot sizes to achieve ablation. This problem is solved by the current invention, which also enables direct contact via fibre delivery for the smallest spot size and least amount of energy on target possible. The relaxation of long working distances to accommodate high flow water cooling is a very important feature of the invention. The ability to bring a fibre into close contact or close positioning of a fibre to the affected area also ensures a flat top beam profile to further minimize collateral damage to regions outside the ablated area. In the near field region at the fibre exit of a metallized hollow fibre the intensity profile is uniform and the absorption in the IR region is so strong as to produce strong localization of the absorbed energy in this near field region. The feature enables a simple means to attain a spatially uniform radial profile of heat distribution as shown as optimal in FIG. 11. This approach can be adopted using other fibre optics and waveguiding devices with large index of refraction differences or structured index of refraction profiles that give good approximations to flat top intensity profiles in the near field as a simple means to deliver flat top intensity profiles on target.

These new methods presented here, enable higher cutting speeds, reduction of collateral damage to its lowest possible value for acceptable outcomes, and direct contact or close coupling of the laser beam delivery system by way of focusing elements or fibre optics or other waveguiding devices to target. The invention covers optimal performance with respect to temporal, wavelength and spatial aspects of short IR pulse beam delivery for minimally invasive removal of material.

The method disclosed herein is particularly advantageous for laser removal of tissue, such as but not limited to, dental tissue including tooth dentin, enamel and gum tissue, corneal tissue, skin, all human organs, connective tissue, muscular tissue, vascular tissue, nerves, urological tissue, glandular tissue, endocrine tissue, and bone tissue.

At the opposite extreme of laser pulse durations, patents covering laser cutting and material processing have been issue [6, 7]. In all these patents, the use of ultrashort pulses is defined to be in the femtosecond to picosecond range and exploit cutting mechanisms based on multiphoton absorption for energy localization and/or plasma formation. In both cases, ionizing effects occur that cause damage to adjacent materials. In the case of metals, the ions are quickly quenched by mobile charge in the metals. However, semiconductors are more sensitive to ions affecting doping profiles.

For medical and dental applications, the occurrence of ionization in the ablation process leads to damage of the surrounding tissue and destruction of biological pathways. The new concepts put forward in this patent application detail that there are optimal pulse durations and that ultrashort pulses as defined above do not necessarily meet these conditions. Moreover, the cutting mechanism disclosed herein is clearly distinguished from all ultrashort pulse patents. The ultrashort pulse ablation mechanisms rely on multiphoton absorption to generate short lived excited electrons and ions that rapidly deposit energy into heat. Whereas, the method disclosed herein teaches how to impart heat to a material as fast or faster than even these ultrashort pulse multiphoton processes by coupling the light energy directly to mechanical degrees of freedom (heat) via exciting vibrations. This new avenue for laser driven ablation, as defined based on 1-photon vibrational resonances, enables molecular level tuning for selective cutting well beyond anything possible with nondiscriminate multi-photon absorption mechanisms leading to ionization. The vibrational spectrum of molecules is a signature of that molecule and by using specific IR wavelengths matched to this molecule permits molecular level control of the heat deposition and subsequent cutting.

Basically, prior to this invention there was no single laser processing procedure for cutting that avoided significant collateral damage either in the way of excessive thermal damage or ionizing radiation damage to adjacent zones. The problem is most pronounced in the application to medical and dental fields where there are soft materials involved and there is a delicate balance of chemistry and composition that is very sensitive to heat and ionization effects. This invention provides a universal solution to crafting optimal laser pulses for cutting to provide minimal collateral damage. In the case of medical and dental applications, this invention offers the first laser processing method for cutting at precisions well beyond any mechanical tool (scalpel, etc.) with complete healing. In fact, healing times should approach fundamental limits in that cutting can be done at the single cell level of precision, smallest possible wound sizes, to permit maximum healing rates. There is thus enormous socioeconomic impact of this invention.

EXAMPLE

To optimally cut tissue for medical applications, the laser pulse should be tuned to the water absorption lines. Water is the largest single component in the chemical composition of biological tissue. The absorption processes of water are strongest in the IR and near VUV. Of the two wavelength regions, the IR is preferred as the UV will be absorbed by other materials before hitting the target area and cause deleterious photochemistry. The strongest absorption bands in water are related to the OH symmetric stretch (3400 cm$^{-1}$) and OH bending motions (1650 cm$^{-1}$). The absorption is so strong that the 1/e penetration depth in pure water is 0.75 μm. The OH bend is similar in absorption strength. The pulse duration in this case should be less than 1 ns and ideally should be between 1 to 100 ps. Shorter pulses will lead to multiphoton absorption effects and deleterious ion formation. The temperature of the lattice should be superheated to above the vaporization point of the constituent material.

Most constituents in tissue go into the gas phase at 100° C. (water) to 1000° C. (biopolymers). The energy threshold to achieve this temperature jump with a 1 μm absorption depth is approximately 1 J/cm$^2$. For 1 ps pulses or less, much of the energy will reside in excited vibrations longer than the pulse duration. This energy threshold corresponds to approximately twice as many IR photons as absorbers such the material's absorption will be effectively bleached and the optical penetration depth will be extended by this bleaching process, deeper than the intrinsic low fluence absorption depth. This bleaching effect increases the laser energy threshold for ablation and leads to excess heating and damage. In this scenario, the optimal laser pulse is constructed of approximately 50% of the energy tuned to wavelengths corresponding to the OH stretch and half to the OH bend. The energy will be delivered to the smallest possible volume element for a given laser beam focus. Other wavelengths can be similarly multiplexed to increase the energy deposition by minimizing the bleaching effects. This optimization process effectively spreads the energy out in the spectrum to increase the available accepting modes for the laser energy to most strongly localize a given amount of energy.

Similar to the above, for laser cutting biological tissue with a large fraction of fibrous material, the laser cutting is optimized by providing additional laser energy tuned to the amide vibrations of the fibril (e.g. collagen) to soften the polymer. This latter exposure should be provided ahead of the main laser pulse providing the temperature jump for vaporization and vapour front driven ablation. This example would involve a laser pulse or series of pulses in which the first part of the energy is selectively tuned to heat up the collagen (or other material with a higher temperature than water for a phase transition), followed with an optimized waiting time for polymer softening, ideally to heat the polymer above the glass temperature, and then the major blast to drive ablation. In this scenario, the laser pulse could have the optimized pulse tuned to the water transitions and the biopolymer. The final laser ablation pulse would optimally follow the above guidelines with respect to pulse duration.

All combinations of resonant 1-photon pathways for wavelength multiplexing the pulse energy and tuning the pulse temporal profile, which lead to material ablation faster than thermal transport by either diffusion or acoustic propagation to adjacent regions, should be covered. The ideal laser source is tuneable in the IR with sufficient power to deliver above threshold pulse energies, e.g. reference 22.

In Summary, the present invention provides a method of laser processing of materials that is based on a new understanding of the ablation process and the dynamics of energy transduction of vibrational energy into heat. The invention disclosed herein provides a new methodology in which one can efficiently achieve material ablation with the minimum of collateral damage through either ion formation or thermal accumulation. This is accomplished by impulsive heat deposition (IHD), a novel method that combines both thermally and photomechanically driven ablation mechanisms, in which most of the absorbed energy remains in the ablated material. The laser energy is effectively coupled directly to the mechanical degrees of freedom that lead to ablation and in so doing performs this task at optimal efficiency, which is key to minimizing collateral damage.

For pulse durations greater than the time required for thermally driven expansion the mechanism of ablation will be dominated by "phase explosion" [8, 9]. For pulse durations shorter than the thermally driven expansion time and energy deposition below the vaporization threshold, photomechanical effects dominate [3, 4, 10]. But with energy deposition between the vaporization threshold and the plasma formation threshold, and with pulse durations that are shorter than the thermally driven expansion time, impulsive heat deposition (IHD) will occur, resulting in ablation with minimal collateral damage.

When the pulse duration is longer than thermally driven expansion time, only the "phase explosion" mechanism contributes to ablation. In addition to superheating of the lattice material, the deposited energy will also lead to the generation of strong acoustic waves, which can propagate beyond the irradiated volume during the laser pulse. Acoustic propagation out of the irradiated zone represents energy lost to the ablation process and lowers the efficiency for ablation. The strong acoustic wave propagation will also result in stresses, and associated damage in adjacent material that is greater than if both photomechanical and phase explosion are coupled constructively to drive the ablation process, as in the present invention. In addition, the acoustic propagation out of the irradiated zone for pulse durations longer than thermally driven expansion time, or impulsive limit, leads to excess heating of the surrounding material through acoustic attenuation/absorption.

This amount of energy can be a significant fraction of the total deposited energy. For example, within linear response, the acoustic term leads to strain in the material that is approximately equal to that of thermally induced strain. See for example Genberg et al., [11] in which the thermo-elastic equations of motion for arbitrary thermalization or heating rates were solved analatycally for the first time for an exact solution to the thermally induced strain and stresses in materials. The propagation of this acoustic energy out of the laser heated targeted zone, at the limit of strong excitation and shock wave formation, can cause collateral damage to the adjacent material. This prospect is to be avoided by using IHD in which both the confinement stresses or photomechanical mechanism and thermal mechanism driven by superheating and phase transformation under inertial confinement lead to ablation faster than acoustic propagation out of the heated zone.

With IHD disclosed herein, a "cold ablation" process is achieved by depositing the energy impulsively into heat within the target zone. This impulsive heat deposition leads to large stresses under approximate constant volume conditions or stress confinement of the energy. The high lattice temperatures also create conditions for void creation and cavitation effects as the material passes rapidly through phase transitions from solid to liquid and vapour as it is heated. The void spaces and cavitation stresses arise from random homogeneous nucleation processes for the phase changes that grow exponentially in number and size with temperature [12].

The confinement of thermal expansion and stresses associated with void formation and cavitation through homogeneous nucleation are confined in the strongly heated surface region. The subsequent material response is to undergo rapid expansion against the inertial confinement of the unheated bulk material in relation to the minimal resistance of the free surface. The material goes beyond its adhesion forces and material is ablated from the surface region. By confining the energy inertially through IHD, nearly all the energy becomes stored as potential energy and is converted into translational kinetic energy in the ablation process.

It is in this sense that the ablation is referred to as a cold ablation process. The ablation is fundamentally derived from thermally driven confinement stresses and released by virtue of the close proximity of this force to a free surface and in so doing leaves very little energy behind as heat in the surrounding material. It is important to realize that there are two source terms for the forces driving the ablation. One is the collective stress confinement that is released upon the explosive thermal expansion of a superheated material. This source term is referred to as the photomechanical stress or force. The other source is from the homogeneous nucleation phenomena unique to these high pressure and temperature conditions that lead to additional stresses in the material through void formation and cavitation from rapid heating. This latter effect is a consequence of the lattice temperature in relation to the phase diagram of the material under the metastable conditions of impulsive superheating. This force will be referred to a thermally derived mechanism as it pertains to equation of state changes as apposed to a direct relation to thermal expansion forces. Both of these source terms constructively interfere to drive ablation in the IHD mechanism.

The rate of superheating needs to be sufficient to drive the phase transitions faster than acoustic propagation out of the heated zone as described above. In this manner all of the forces from the photomechanical and thermal mechanisms are inertially confined and released in a highly directed manner through displacement of the free surface that leads to ablation. This mechanism is distinct from heating on longer timescales that allow expansion of the material and exploit the stresses created during phase changes referred to as phase explosion to drive ablation [ref. 13. E. Leveugle, D. S. Ivanov, and L. V. Zhigilei, "Photomechanical spallation of molecular and metal targets: molecular dynamics study", Applied Physics A 79,1643-1655 (2004)].

This latter mechanism does not exploit stress confinement as the material is allowed to expand [ref E. Leveugle et al. 13]. The IHD mechanism disclosed herein is much more efficient. Simply put, energy in driving the ablation through IHD is not lost through thermal expansion that leads to both cooling and reduction in the induced stresses. As such this mechanism is distinct from other patents covering the use of infrared lasers for material processing as derived from ablation [9.10, 14].

The problem has been developing a means to create conditions for IHD without involving deleterious side effects such as unwanted photochemistry or multiphoton ionization; side effects equally damaging to surrounding material as excess heating effects. Even theoretical calculations exploring the different forces involved in laser superheating of highly idealized model systems, used UV excitation at 337 nm of electronic states in the model calculations to provide strong absorption [Leveugle et al 13]. It was assumed that such excited electronic states would rapidly relax this energy into vibrations (which is not the case, excited electronic state lifetimes are typically many ns). The use of UV light would lead to extensive ionization as well as extensive photochemistry in real systems for sufficiently short pulses for impulsive excitation conditions and further illustrates that a means to strongly localize the light and achieve IHD without deleterious side effects was not known prior to this work. This invention describes a method to create IHD that solves this problem through a combination of short lived vibrational modes and strong spatial localization of the absorbed light. The use of vibrational modes provides a mechanism to deposit energy directly into mechanical degrees of freedom without involving electronic states that lead to photochemistry or multiphoton absorption that leads to ionizing effects. In this direct drive case, the pulse duration of laser radiation tuned to vibrational modes is less than the time required for acoustic waves to traverse the irradiated volume. Since the acoustic waves will largely be confined to the ablated volume, the induced stresses will no longer strongly impact the surrounding material and less collateral damage will occur. All the deposited energy remains in the target zone to drive ablation. IHD also leads to the formation of shockwaves inside the irradiated volume. A considerable advantage of this method is the enhanced efficiency of the ablation, especially in heterogeneous materials such as living tissue, which results from the effect of these photomechanical shockwaves on the material properties of the irradiated volume. The heterogeneous nature of living tissue leads to microscopic regions in which there are constituent components with locally significantly lower vapour phase transition temperatures that seed void formation and cavitation stresses. Microscopic pools of water in living tissue provide ideal source terms to drive ablation at lower input energies. The improved efficiency of IHD, through stress confinement and exploitation of rapid homogeneous nucleation under such conditions, leads to less collateral damage and an effectively gentler ablation process with respect to the affect on the surrounding material. Thus IHD offers a superior mechanism for the ablation of materials such as biological tissues which are particularly sensitive to thermal and acoustic damage.

The dramatic advantages of this new cutting mechanism are shown in FIG. 2 in which femtosecond laser pulses at 795 nm excitation are directly compared to short IR pulses that are tuned to the absorption wavelength of the O—H stretch in water. One sees that in the case of IHD using IR wavelengths tuned to OH stretch region whole fibres are ejected intact from the bone sample (FIGS. 2B to 2D). In contrast, the femtosecond laser ablation leads to smooth surfaces (FIG. 2A) demonstrating complete disintegration of the integrity of the ablated material. These observations clearly demonstrate the less destructive nature of IHD compared to multi-photon absorption into electronic states used by femtosecond ablation.

This patent pertains to methodologies to exploit specifically the deposition of energy into heat through selective excitation of molecular vibrations. The strong localization of light energy into short lived vibrational modes that couple directly to heat without ion formation is the key enabling concept, along with a proper prescription for the time course for depositing the energy to avoid collateral thermal and acoustic damage. This concept also enables a high degree of selectivity by tuning the laser wavelengths to match the target material, even to the point of molecular selectivity.

This molecular selectivity by wavelength tuning of the laser is particularly advantageous when trying to remove a single specific material from a target. Important applications include removing tumour cells that have specific spectral markers or only removing dental caries selectively from good tooth matrix. These are just two important examples.

The pulse duration needs to be long enough to prevent peak intensities which will cause multiphoton absorption so that the effects of ionizing radiation are avoided. The optimal pulse range to satisfy these conditions is between 1 picosecond (ps) and 1 nanosecond (ns). Previous patents [6, 7, 9-10] on pulsed laser ablation do not acknowledge this temporal window in which IHD occurs for minimum collateral damage. All prior art has either used wavelengths that do not directly couple to molecular vibrations (femtosecond laser based methodology) and ionized material as the principle means of driving ablation [6, 7], or "phase explosion" based on laser technologies that are limited to pulse durations greater than 1 ns (e.g: Er:YAG) to drive ablation outside the IHD domain [9, 10, 14]. Specifically, patents covering the use of femtosecond lasers for ablation [6, 7] exploit the high peak powers of such short pulses to ionize material, generate free electrons, and ultimately plasma formation.

One patent [6] states that the high peak power ($>10^{12}$ W/cm$^2$) of such pulses is used to directly convert solid to an ionized plasma to drive ablation through hydrodynamic expansion of the plasma. The other patent in this domain [7] also exploits ionization of the material and generation of high density of free electrons ($>10^{18}$ electrons/cm$^3$) to absorb energy from the field, undergo avalanche ionization to form a plasma, material disintegration and ablation. This latter patent [7] also identifies a pulse regime below 10 ps for which the ablation threshold shows a significant deviation from a square root dependence, indicative of a deterministic process for plasma formation.

The present invention excites vibrations of the constituent material to deliver heat and use IHD to directly drive the ablation process, rather than multiphoton excitation of electronic states and ionization in order to deliberately avoid ionized plasma formation. The central concept behind the present invention is to completely avoid or minimize as much as possible ionization effects. The IHD mechanism presented here relies on energy being deposited as heat faster than thermal expansion of the heated zone. For pulses below this time period and longer than that leading to multiphoton ionization, there is only a weak pulse duration dependence that is related to the decrease in cancellation of the acoustic strain from the leading edge of the pulse as described in acoustic excitation by heat pulses [ref. Genberg et al as above 11].

In any case, under strong 1-photon absorption conditions of the present invention there is no square root dependence on the pulse duration in the first place to which a deviation can be observed. These distinguishing features emphasize the key fundamental differences in the ablation mechanism between femtosecond laser based approaches and IHD using IR wavelengths for direct drive ablation. The other related patents that use IR to excite vibrations as the means to energize the material specifically exclude pulse durations shorter than 1 ns [9, 10] and as such do not satisfy conditions for IHD. These patents exploit exclusively phase explosions [9] and failed to realize that significantly higher stresses or forces are generated for a given amount of absorbed energy under inertial confinement conditions only realized under IHD.

The specific omission of pulses less than 1 ns was given as the domain of operation [10] as it was believed that inertial confinement was not necessary and that short pulses in this domain would lead to shock wave induced damage [4]. The concept of shock wave induced damage permeates the laser ablation literature [1] and these other patents are consistent with the idea that slower heating rates are needed to avoid shock wave formation.

These patents and all related prior art failed to recognize that phase changes occur equally well under inertial confinement or high pressures as in the case of thermally relaxed expanded materials and with more explosive force. The stresses from the associated volume changes with phase transitions add constructively to the collective thermal expansion or photomechanical forces. Equally important, in the IHD limit, the ablation occurs faster than significant acoustic propagation; most of the energy goes into ablation and in the process greatly reduces shock wave amplitudes to the same degree or more as ablation with longer pulses.

Once the threshold for ablation occurs, the whole process occurs very quickly in either IHD or with slower heating rates and it is this step that dominates shock wave formation. The key to minimizing collateral damage is to localize the energy spatially as strongly as possible to prevent energy transfer to adjacent zones by whatever transduction mechanism. The IHD mechanism is the one mechanism that completely confines all the absorbed laser energy and most efficiently channels this stored energy into ablation. For technical reasons, these patents also failed to recognize IHD in that it is only very recent that solid state laser technology has advanced to the stage that it is now possible to generate pulses in the IR that are short enough (<1 ns) and with enough energy [22] to achieve IHD ablation as described above. In either case, concepts employing shorter IR pulses were not considered in these previous patents [9, 10] as it was not the operative mechanism of these aforementioned ablation concepts. This invention embodies the first demonstration of resonant or direct drive ablation using IR excitation in the 1-1000 ps pulse duration regime with minimal collateral damage using IHD, and as such has also reduced the concept to practice for the first time.

TABLE 1

Speed of sound in different tissues

| Tissue | Sound Velocity (m/s) |
|---|---|
| Air | 330 |
| Fat | 1450 |
| Human tissue (mean) | 1540 |
| Brain | 1541 |
| Blood | 1570 |
| Skull bone | 4080 |
| Water | 1480 |

This table is included to provide some representative physical parameters to define the required laser parameters as discussed in the text.

As used herein, the terms "comprises" and "comprising" are to be construed as being inclusive and open ended, and not exclusive. Specifically, when used in this specification including claims, the terms "comprises" and "comprising" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

1. A. Vogel and V. Venugopalan. "Mechanisms of pulsed laser ablation of biological tissues." *Chemical Reviews* 103.2 (2003): 577-644.
2. D. R. Ermer, M. R. Papantonakis, M. Baltz-Knorr, D. Nakazawa, R. F. Haglund, "Ablation of dielectric materials during laser irradiation involving strong vibrational coupling", *Appl. Phys. A* 70 (2000): 633.
3. R. S. Dingus, R. J. Scammon, "Grüneisen-stress induced ablation of biological tissue" *Proc. SPIE* 1427 (1991): 45.
4. H. J. Hoffman, W. B. Telfair, "Minimizing thermal damage in corneal ablation with short pulse mid-infrared lasers" *J. Biomed. Opt.* 4.4 (1999): 465.
5. F. H. Loesel, M. H. Niemz, J. F. Bille, T. Juhasz "Laser-induced optical breakdown on hard and soft tissues and its dependence on the pulse duration: Experiment and model." *IEEE J. Quant. Elect.* 32.10 (1996): 1717-22.
6. M. D. Perry, B. C. Stuart, "Ultrashort pulse laser machining of metals and alloys", U.S. Pat. No. 6,621,040 (2003).
7. G. A. Mourou, et al. "Method for controlling configuration of laser induced breakdown and ablation", U.S. Pat. No. 5,656,186 (1997).
8. R. Kelly, A. Miotello, "Contribution of vaporization and boiling to thermal-spike sputtering by ions or laser pulses", *Phys. Rev. E* 60 (1999):2616
9. R. F. Haglund, D. Ermer, "Method and apparatus for laser ablative modification of dielectric surfaces" US Patent application No. 20040195221(2004).

10. W. B. Telfair, P. R. Yoder, H. J. Hoffman, "Method and apparatus for removing corneal tissue with infrared laser radiation", U.S. Pat. No. 5,782,822 (1998)
11. L Genberg, Q. Bao, S. Gracewski, and R. J. D. Miller, "Picosecond Transient Thermal Phase Grating Spectroscopy—A New Approach to the Study of Vibrational-Energy Relaxation Processes in Proteins," Chem. Phys., 131 (1989) 81
12. B. Rethfeld, K. Sokolowski-Tinten and D. von der Linde "Ultrafast thermal melting of laser-excited solids by homogeneous nucleation", Phys. Rev. B 65.9 (2002):092103.
13. E. Leveugle, D. S. Ivanov, and L. V. Zhigilei, "Photomechanical spallation of molecular and metal targets: molecular dynamics study", Appl. Phys. A 79, (2004) 1643
14. D. Boutoussov, C. Cozean, "Method of corneal sculpting using a laser", U.S. Pat. No. 6,824,541 (2004).
15. B. Jean, T. Bende, "Mid-IR Laser Applications in Medicine", Topics. Appl. Phys. 89 (2003):511
16. M. L. Cowan, B. D. Bruner, N. Huse, J. R. Dwyer, B. Chugh, E. T. J. Nibbering, T. Elsaesser, R. J. D. Miller, "Ultrafast memory loss and energy redistribution in the hydrogen bond network of liquid H2O", Nature, 434, (2005):199.
17. C. Schmuttenmaer, C. C. Miller, J. Herman, J. Cao, Y. L. Gao, D. Mantell, R. J. D. Miller, "Femtosecond time-resolved photoemission study of hot electron relaxation at the GaAs(100) surface", Chem. Phys. 205 (1996):91.
18. R. J. D. Miller, "Vibrational-energy relaxation and structural dynamics of heme-proteins", Ann. Rev. Phys. Chem. 42 (1991):581.
19. D. D. Dlott, M. D. Fayer, "Application of a 2-color free-electron laser to condensed matter molecular dynamics", J. Opt. Soc. Am. B 6.5 (1989):977.
20. Copending U.S. patent application Ser. No. 60/704,905 filed Aug. 3, 2005 entitled "Hybrid ultrafast laser surgery-growth factor stimulation for ultraprecision surgery with healing"
21. See FIG. 2 in: G. Edwards et al., "Tissure ablation by a free-electron laser tuned to the amide II band", Nature 371 (1994):416.
22. R. J. D. Miller, K. Franjic, D. Kraemer, M. Piche, "Method and apparatus for high power optical amplification in the infrared wavelength range (0.7-20 mum)", US Patent application Publication 20050271094. (2005).

Therefore what is claimed is:

1. A method of laser processing of a material, comprising the steps of:
   i) identifying at least one component of a material to be laser processed and selecting a pulsed laser to produce laser pulses having a wavelength such that the laser pulses are absorbed by the at least one component, and adjusting the pulsed laser to produce the laser pulses having an energy sufficient such that each laser pulse absorbed in a volume of the material irradiated by the laser pulses produces superheated temperatures above a vaporization point of said at least one component of material contained in the laser irradiated volume,
   ii) selecting a pulse duration time that meets requirements for impulsive heat deposition such that each pulse duration time is made shorter than a time required for thermal diffusion out of the volume and made shorter than a time required for a thermally driven expansion of the volume, and such that the pulse duration time is made long enough and the pulse energy is made low enough so that a peak intensity of each laser pulse is below a threshold for ionization driven ablation to occur in the material, such that most of the energy contained in each laser pulse will be converted to ablation of the material out of the volume with any residual energy not being enough to substantially damage material surrounding the volume irradiated by the pulsed laser; and
   irradiating the volume of the material with the pulsed laser to laser process the material.

2. The method according to claim 1 wherein the wavelength of each of the laser pulses lie between 1.5 and 20 microns.

3. The method according to claim 2 wherein the pulsed laser beam wavelength is selected to produce at least one excited state in the material that has a lifetime shorter than the pulse duration requirement in step ii).

4. The method according to claim 3 wherein each of said laser pulses contain a pre-selected range of wavelengths to give selective tuning of the laser radiation to the material properties by both peak power and wavelength to produce strong absorption conditions.

5. The method according to claim 3 wherein each of said laser pulses contain a pre-selected range of wavelengths corresponding to a maximum absorption of at least one constituent of said material to be ablated, such that the absorbed energy is localized as strongly as possible.

6. The method according to claim 4 wherein each of said laser pulses contain a pre-selected range of wavelengths chosen to give 1-photon resonance absorption to minimize multiphoton processes and ionization.

7. The method according to claim 3 wherein each of said laser pulses contain a pre-selected range of wavelengths chosen to give one or multiple transitions within the same absorption band to maximize the absorbed energy per unit volume or mass with respect to a surface of said volume of material.

8. The method according to claim 3 wherein each of the laser pulses contain a pre-selected range of wavelengths tuned to two or more different absorption bands of constituents of said material to wavelength multiplex delivery of energy for maximizing delivery of energy absorbed/unit volume or mass.

9. The method according to claim 3 wherein the pulsed laser beam is pulsed and scanned spatially in such a way so that the time intervals between each of the laser pulses impacting on the same laser irradiated volume are longer than the thermal diffusion time in either lateral or longitudinal directions in the material to avoid heat accumulation and heat induced damage.

10. The method according to claim 3 wherein the pulse duration is between about 1 and about 1000 ps.

11. The method according to claim 3 including shaping each of the laser pulses in temporal and spectral domains in order to reduce effects of bleaching and ionization in the laser irradiated volume.

12. The method according to claim 11 wherein each of the laser pulses are shaped so that they contain spectrally shifted components occurring later in each laser pulse, corresponding in time to dynamically shifting absorption bands of the material due to excited state creation and heating of the material by said laser pulses.

13. The method according to claim 11 wherein each of the laser pulses are shaped into a burst of sub-pulses, where a time interval between the sub-pulses is greater than the thermal relaxation time of the excited states, and wherein an envelope of the burst of sub-pulses satisfies the pulse duration requirements of steps ii) and iii).

14. The method according to claim 3 wherein the said irradiated volume of material contains biological tissue.

15. The method according to claim 14 wherein the wavelength of each of the laser pulses is tuned to water absorption lines in said tissue such that said at least one component of material which is superheated to temperatures above a vaporization point is water.

16. The method according to claim 15 wherein said water absorption lines are related to the OH symmetric stretch (3400 cm$^{-1}$ spectral region) and/or OH bending motions (1650 cm$^{-1}$ spectral region).

17. The method according to claim 14 wherein said wavelengths of each of the laser pulses are tuned to vibrational absorption lines corresponding to amide and phosphate absorption bands.

18. The method according to claim 14 including a step of irradiating said volume of tissue for an effective length of time with laser pulses having desired molecular or material selectivity to produce desired changes in properties of the tissue prior to, or simultaneously with said step of irradiating said volume of tissue with said pulsed laser beam.

19. The method according to claim 18 wherein said desired changes in properties of the tissue enhance the ablation process, including any one of softening, melting or breakage of collagen fibrils or other connective tissue.

20. The method according to any of claim 1 wherein said material is selected from the group consisting of polymers, semiconductors, metals, plastics or glasses, or any heterogeneous combination thereof.

21. The method according to claim 3 including shaping each of said laser pulses to have a spatial profile which is substantially flat top to give a uniform spatial intensity profile to further minimize heating of regions of the material that do not reach a threshold for ablation.

22. The method according to claim 3 in which each of the laser pulses are delivered to said irradiated volume of material using a waveguiding element.

23. The method according to claim 22 wherein said waveguiding element is selected from the group consisting of hollow fibres, holey fibres, photonic crystal fibres, and spatially profiled index of refraction fibre optics, and wherein said waveguiding element is placed close enough to said volume of tissue being irradiated so that each of said laser pulses exiting from said waveguiding element are in a near field region having an intensity profile which is approximately flat top and are absorbed by said tissue before the profile changes to that characteristic of a far field region.

24. A method of laser surgery on tissue, comprising:
i) identifying at least one component of tissue to be laser processed and selecting a pulsed laser to produce laser pulses having a wavelength such that the laser pulses are absorbed by the at least one component, and adjusting the pulsed laser to produce the laser pulses having an energy sufficient such that each laser pulse absorbed in a volume of the tissue irradiated by the laser pulses produces superheated temperatures above a vaporization point of said at least one component of tissue contained in the laser irradiated volume of tissue,
ii) selecting a pulse duration time of said laser pulses that meets requirements for impulsive heat deposition such that each laser pulse duration time is made shorter than a time required for thermal diffusion out of the laser irradiated volume of tissue and shorter than a time required for a thermally driven expansion out of the laser irradiated volume of tissue, and such that the pulse duration time is made long enough and the pulse energy low enough so that a peak intensity of each laser pulse is below a threshold for ionization driven ablation to occur in the tissue, such that most of the energy contained in each laser pulse will be converted to ablation of the tissue in the laser irradiated volume of tissue with any residual energy not being enough to substantially damage the tissue surrounding the laser irradiated volume of tissue; and
irradiating the volume of tissue with the pulsed laser to laser process the tissue.

25. The method according to claim 24 wherein wavelengths of each of the laser pulses lie between about 1.5 and about 20 microns and correspond to a strong absorption of at least one constituent of the tissue to be ablated, such that the energy is localized as strongly as possible.

26. The method according to claim 25 wherein wavelengths of each of the laser pulses is tuned to water absorption lines in the tissue.

27. The method according to claim 26 wherein said water absorption lines are related to the OH symmetric stretch (3400 cm$^{-1}$ spectral region) and/or OH bending motions (1650 cm$^{-1}$ spectral region).

28. The method according to claim 25 wherein said wavelengths of each of the laser pulses are tuned to vibrational absorption lines corresponding to amide and phosphate absorption bands.

29. The method according to claims 25 including a step of irradiating said volume of tissue for an effective length of time with laser pulses having desired molecular or material selectivity to produce desired changes in properties of the tissue prior to, or simultaneously with said step of irradiating said volume of tissue with said pulsed laser beam.

30. The method according to claim 29 wherein said desired changes in properties of the tissue enhance the ablation process, including any one of softening, melting or breakage of collagen fibrils or other connective tissue.

31. The method according to claim 25 including shaping each of said laser pulses to have a spatial profile which is substantially flat top to give a uniform spatial intensity profile to further minimize heating of regions of tissue that do not reach a threshold for ablation.

32. The method according to claim 25 in which each of the laser pulses are delivered to said irradiated volume of tissue using a waveguiding element.

33. The method according to claim 32 wherein said waveguiding element is selected from the group consisting of hollow fibres, holey fibres, photonic crystal fibres, and spatially profiled index of refraction fibre optics, and wherein said waveguiding element is placed close enough to said volume of tissue being irradiated so that said laser pulses exiting from said waveguiding element are in a near field region having an intensity profile which is approximately flat top and are absorbed by said tissue before the profile changes to that characteristic of a far field region.

34. The method according to claim 25 wherein the pulsed laser beam is pulsed and scanned spatially in such a way so that the time intervals between each of laser pulses impacting on the same laser irradiated volume of tissue are longer than the thermal diffusion time in either lateral or longitudinal directions in the tissue, to avoid heat accumulation and heat induced damage.

35. The method according to claim 25 including shaping each of the laser pulses in temporal and spectral domains in order to reduce effects of bleaching and ionization in the laser irradiated volume of tissue and thereby reduce damage to surrounding tissue from excess heat or ionization effects transferred to the surrounding area.

36. The method according to claim 35 wherein each of the laser pulses are shaped so that they contain spectrally shifted components occurring later in the pulse, corresponding in time to dynamically shifting absorption bands of constituents of the tissue due to excited state creation and heating of the constituents of the tissue by said laser pulses.

37. The method according to claim 35 wherein each of the laser pulses are shaped into a burst of sub-pulses, where a time interval between the sub-pulses is greater than the thermal relaxation time of the excited states, and wherein an envelope of the burst of sub-pulses satisfies the laser pulse duration requirements of steps ii) and iii).

38. The method according to claim 36 wherein each of the laser pulses are shaped so that they contain spectrally shifted components occurring later in the pulse, corresponding in time to the dynamically shifting absorption bands in the tissue.

39. The method according to claim 15 wherein said tissue is selected from the group consisting of dental tissue including tooth dentin, enamel and gum tissue, corneal tissue, skin, all human organs, connective tissue, muscular tissue, vascular tissue, nerves, urological tissue, glandular tissue, endocrine tissue, and bone tissue.

40. The method according to claim 24 wherein said tissue is selected from the group consisting of dental tissue including tooth dentin, enamel and gum tissue, corneal tissue, skin, all human organs, connective tissue, muscular tissue, vascular tissue, nerves, urological tissue, glandular tissue, endocrine tissue, and bone tissue.

41. The method according to claim 24 wherein the pulse duration is about 100 ps.

* * * * *